(12) United States Patent
Takahashi et al.

(10) Patent No.: US 9,547,218 B2
(45) Date of Patent: Jan. 17, 2017

(54) LENS MODULE AND PORTABLE PHOTOGRAPHY DEVICE

(71) Applicant: HITACHI MAXELL, LTD., Ibaraki-shi, Osaka (JP)

(72) Inventors: Takehiro Takahashi, Ibaraki (JP); Akito Sakemoto, Ibaraki (JP); Hiroyasu Otsubo, Ibaraki (JP)

(73) Assignee: HITACHI MAXELL, LTD., Osaka (JP)

( * ) Notice: Subject to any disclaimer, the term of this patent is extended or adjusted under 35 U.S.C. 154(b) by 0 days.

(21) Appl. No.: 14/758,326

(22) PCT Filed: Dec. 20, 2013

(86) PCT No.: PCT/JP2013/084327
§ 371 (c)(1),
(2) Date: Jun. 29, 2015

(87) PCT Pub. No.: WO2014/103954
PCT Pub. Date: Jul. 3, 2014

(65) Prior Publication Data
US 2015/0355527 A1    Dec. 10, 2015

(30) Foreign Application Priority Data

Dec. 27, 2012    (JP) ................................ 2012-284670

(51) Int. Cl.
*G03B 15/05*    (2006.01)
*G02B 13/24*    (2006.01)
(Continued)

(52) U.S. Cl.
CPC ................ *G03B 15/05* (2013.01); *A61B 5/00* (2013.01); *F21L 4/02* (2013.01); *F21V 23/0414* (2013.01);
(Continued)

(58) Field of Classification Search
CPC ...... H04N 5/2254; H04N 5/238; H04N 5/225; H04N 5/2251; H04N 5/23293; H04N 5/2256; H04N 5/2257; G03B 15/05; G03B 15/03; G03B 17/56; G03B 13/24; G03B 17/565; G03B 17/14; G03B 2215/0589; G03B 2215/0567; A61B 5/00; F21L 4/02; F21V 23/0457; F21V 23/0414; F21Y 2101/02

See application file for complete search history.

(56) References Cited

U.S. PATENT DOCUMENTS

2006/0251408 A1    11/2006  Konno et al.
2009/0002485 A1     1/2009  Fujiwara
2012/0230663 A1*    9/2012  Ogasawara .............. G03B 7/16
                                                        396/56

FOREIGN PATENT DOCUMENTS

CN          1910431 A      2/2007
EP          1 707 928 A1  10/2006
(Continued)

OTHER PUBLICATIONS

Feb. 10, 2014 Written Opinion issued in International Patent Application No. PCT/JP2013/084327.
(Continued)

*Primary Examiner* — Timothy J Henn
(74) *Attorney, Agent, or Firm* — Oliff PLC

(57) ABSTRACT

Provided is portable photography device capable of appropriately control an on/off state of a light source during photography, and reliably carrying out photography by a camera of a portable terminal when the light source is on. The portable photography device includes a smartphone with a camera, and a lens module including LEDs, having different wavelengths, a conversion lens, and light source control unit. The smartphone includes light on/off detection unit that detects the on/off state of each of the LEDs,
(Continued)

photography control unit that controls photography by the camera, and display control unit that associates a photographed image taken by the camera with the LEDs, for display on the screen of the smartphone. As a result, it is possible to appropriately control the on/off state of the LEDs, during carrying out photography and reliably photographing skin with the camera of the smartphone.

15 Claims, 18 Drawing Sheets

(51) Int. Cl.
  *F21V 23/04* (2006.01)
  *F21L 4/02* (2006.01)
  *H04N 5/232* (2006.01)
  *H04N 5/225* (2006.01)
  *G03B 17/14* (2006.01)
  *G03B 17/56* (2006.01)
  *H04N 5/238* (2006.01)
  *A61B 5/00* (2006.01)
  *F21Y 101/00* (2016.01)

(52) U.S. Cl.
  CPC .......... *F21V 23/0457* (2013.01); *G02B 13/24* (2013.01); *G03B 17/14* (2013.01); *G03B 17/565* (2013.01); *H04N 5/225* (2013.01); *H04N 5/2251* (2013.01); *H04N 5/2254* (2013.01); *H04N 5/2256* (2013.01); *H04N 5/2257* (2013.01); *H04N 5/238* (2013.01); *H04N 5/23293* (2013.01); *A61B 5/0075* (2013.01); *A61B 5/441* (2013.01); *A61B 2560/0443* (2013.01); *F21Y 2101/00* (2013.01); *G03B 2215/0567* (2013.01); *G03B 2215/0589* (2013.01)

(56) References Cited

FOREIGN PATENT DOCUMENTS

| | | |
|---|---|---|
| JP | 2002-009879 A | 1/2002 |
| JP | 2002-232769 A | 8/2002 |
| JP | 2010-160286 A | 7/2010 |
| JP | 2012-008283 A | 1/2012 |
| WO | 2005/071372 A1 | 8/2005 |

OTHER PUBLICATIONS

Feb. 10, 2014 International Search Report issued in International Patent Application No. PCT/JP2013/084327.
Mar. 24, 2016 Office Action issued in Taiwan Patent Application No. 102148463.
Jun. 17, 2016 Search Report issued in European Patent Application No. 13866872.8.

* cited by examiner

LENS MODULE AND PORTABLE PHOTOGRAPHY DEVICE

TECHNICAL FIELD

The present invention relates to a lens module that is removably installed to a portable terminal including a camera, and also relates to a portable photography device including such a lens module and the portable terminal.

BACKGROUND ART

A conversion lens installed on an electronic device including a portable camera, such as a portable phone (including a smartphone) with camera or a tablet-type electronic device with camera, has been known (e.g., see Patent Literature 1).

By installing such a conversion lens on a lens (master lens) on the side of the electronic device, the focal length of the lens can be changed to the wide angle side or the telescope side even when the lens of the portable electronic device is a fixed focus lens. Alternatively, a lens having a close-up function (macro photographing function) may be used as the conversion lens to allow macro photography.

Meanwhile, a camera for skin for photographing skin of a face in a magnified manner to analyze the state of the skin has also been known. A conversion lens having a function of the camera for skin, such as an object magnification and close-up function, added to the camera of the portable phone or the like has also been known. In this case, it can be realized easily to send a photographed image of the skin by mail or the like to the company who analyzes the skin image and receive a result of the skin analysis by mail or the like.

CITATION LIST

Patent Literature

Patent Literature 1: JP 2012-8283 A

SUMMARY OF INVENTION

Technical Problem

The conversion lens that allows the portable phone to have the photographing function of the skin is configured to approach to the skin to take a close-up photo (macro photography). The portable phone or smartphone often includes a flash apparatus that uses an LED as a light source to provide illumination during photography with a camera. The LED used in this flash apparatus is typically set to illuminate an object located at about 1 m apart from the camera with a proper quantity of light.

When such a flash apparatus is used to carry out close-up photography with the conversion lens, the LED of the flash apparatus comes too close to the object, and interrupts uniform illumination of the skin as the object or otherwise causes overexposure of the photographed image due to extremely bright illumination. It may be possible to photograph the skin with natural light, or indoor illumination without using the flash apparatus, but such lighting is likely to be largely changed according the situation.

By considering these problems, it can be considered to provide a flash apparatus suitable for macro photography in the conversion lens. In this case, a built-in battery is provided in the flash apparatus as a power source of the LED which is used as a light source of the flash apparatus. A power switch is also provided such that a user turns on the power switch at the start of the photographing operation to emit light and turns off the power switch at the end of the photographing operation to extinguish the light.

When the flash apparatus is used in this manner, the flash apparatus continues to be turned on for relatively long time, instead of emitting light only instantly. This causes an increase of power consumption compared to the case where the light is turned on momentarily as in the typical flash apparatus. As a result, a large size and large capacity battery may be required or replacement timing of the battery may be earlier.

To photograph skin conditions, it is necessary to carry out two types of photography, i.e., an illumination mode (texture mode) photography to capture the surface shape of the skin by mainly using surface reflection light, and an illumination mode (blot mode) photography to capture the inner condition of the skin by removing the surface reflection light.

The present invention has been made in view of the above problems, and an object of the present invention is to provide a lens module installed on a portable terminal with camera, the lens module capable of carrying out multiple types of photography when photographing an object such as skin, and appropriately carrying out on/off control of a light source during photography, and also provide a portable photography device capable of reliably carrying out photography with a camera in a portable terminal when the light source is turned on.

Solution to Problem

To achieve the above object, a lens module according to claim 1 of the present invention is a lens module removably installed on a portable terminal which includes a camera. The lens module includes multiple types of light sources having different wavelengths to emit light to an object, a conversion lens that collects reflection light emitted from the light sources and reflected on the object, and light source control means that carries out on/off control of the multiple types of light sources.

In the present invention, multiple types of light sources having different wavelengths to emit light to the object such as skin are provided to facilitate carrying out several types of photography. By carrying out the on/off control of the light sources by the light source control means, it is able to appropriately carry out the on/off control of the light sources during the photography.

The portable photography device of the present invention includes a portable terminal with camera and the lens module according to claim 1. The portable terminal includes light on/off detection means that detects an on/off state of each of the multiple types of light sources, photography control means that controls photography by the camera when the off state of each of the light sources is detected, and display control means that associates a photographed image taken by the camera according to the control by the photography control means with the types of the light sources and displays the photographed image on the screen of the portable terminal.

In the present invention, when the on state of each of the multiple types of light sources is detected by the light on/off detection means, the photography control means can carry out photography by the camera, while causing the camera to enter a standby state until turning off of the each of multiple types of light sources is detected. As a result, it is possible to photograph the object by the camera using the multiple types of light sources.

Further, since the photographed image taken by the camera is associated with the type of the light source and displayed on the screen of the portable terminal by the display control means, a user can easily confirm the type of the photographed image displayed on the screen.

In the above structure of the present invention, the display control means may associate the photographed image taken by the camera according to the wavelength component with the light source and display the photographed image on the screen of the portable terminal.

According to this structure, the photographed image is thus associated with the light source according to the wavelength component of the photographed image and displayed on the screen. It is not necessary to associate the photographed image with the type of the light source during photography by the camera. Accordingly, there is an advantage that an allowed deviation from a prescribed value of the light source can be increased to suppress the cost of the light source.

Specifically, the light source, such as an LED, to be installed on the lens module needs to be a light source having a smaller deviation from the prescribed value both in the light source for texture photographing and the light source for blot photographing. In practice, however, there is fluctuation in the wavelength of the light source, and a light source having a wavelength closer to the prescribed value should be selected and used. This leads to a cost increase of the light source like an LED, but, according to the above structure, the cost of the light source can be decreased by increasing the allowed deviation from the prescribed value of the light source.

In the above structure of the present invention, the light source control means of the lens module may repeatedly controls the multiple types of light sources to be turned on successively for a predetermined time period and, after all of the multiple types of light sources have been turned on, turn off all the light sources for a predetermined time period. When the light on/off detection means detects the on state of the light source first time after the lighting of all the light sources has been detected, the photography control means controls photography by the camera. Subsequently, the photography control means may control the photography by the camera at predetermined time intervals in synchronization with turning on of the multiple types of light sources.

According to such a structure, the light source control means repeatedly controls the multiple types of light sources to be turned on successively for a predetermined time period and, after all of the multiple types of light sources have been detected, turn on all the light sources for a predetermined time period. When the light on/off detection means detects the lighting of the light source first time after the off state of all the light sources has been detected, the photography control means controls photography by the camera. Subsequently, the photography control means controls the photography by the camera at predetermined time intervals in synchronization with the turning on of the multiple types of light sources. There is an advantage, therefore, that it is possible to reliably carry out photography by the camera of the portable terminal using the multiple types of light sources, while allowing photography using the multiple types of light sources only by detecting the off state of all the light sources and, after the off state, detecting the first lighting of the light source by the light on/off detection means.

In the above structure of the present invention, the light source control means of the lens module may control the multiple types of light sources to be turned on and turned off successively and repeatedly at predetermined time intervals. The light on/off detection means may detect which light source is on by detecting the wavelength of light of each of the light sources. When the light on/off detection means detects the lighting of each of the light sources, the photography control means may control photography by the camera.

As used herein, controlling photography by the camera refers to releasing the shutter of the camera by the photography control means.

According to this structure, when the light source control means controls the multiple types of light sources to be turned on and turned off successively at predetermined time intervals, and when the light on/off detection means detects which light source is on by detecting the wavelength of light of each of the light source, the photography control means controls photography by the camera. Accordingly, it is possible to reliably carry out photography by the camera of the portable terminal using the multiple types of light sources.

In the above structure of the present invention, the light source control means of the lens module may repeatedly controls the multiple types of light sources to be turned on successively for a predetermined time period and, after all of the multiple types of light sources have been turned on, all the light sources are turned off for a predetermined time period. The light source control means may then repeatedly control that, when the light on/off detection means detects the on state of the light source first time after the off state of all the light sources has been detected, the photography control means controls photography by the camera, and when the light on/off detection means detects the off state of all the light sources and then detects which light source is turned on according to the wavelength, the photography control means controls photography by the camera.

According to this structure, the light source control means repeatedly control the multiple types of light sources to be turned on successively for a predetermined time period and, after all of the multiple types of light sources have been turned on, all the light sources are turned off for a predetermined time period. The light source control means then repeatedly controls that, when the light on/off detection means detects the on state of the light source first time after all the light sources have been turned off, the photography control means controls photography by the camera, and when the light on/off detection means detects the off state of all the light sources and then detects which light source is turned on according to the wavelength, the photography control means controls photography by the camera. Accordingly, it is possible to reliably carry out photography by the camera of the portable terminal using the multiple types of light sources, while carrying out photography using each light source at appropriate timing.

The lens module of the present invention according to claim 1 includes transmission/reception means that receives a light-source turn-on instruction signal and a light-source turn-off instruction signal from the portable terminal, while transmitting a light-source turn-on reporting signal and a light-source turn-off reporting signal to the portable terminal.

Upon receipt of the light-source turn-on instruction signal, the light source control means may turn on the light source and cause the transmission/reception means to transmit the light-source turn-on reporting signal to the portable terminal. Upon receipt of the light-source turn-off instruction signal, the light source control means may turn off the light source and cause the transmission/reception means to transmit a light-source turn-off reporting signal to the portable terminal.

According to this structure, the light source control means turns on the light source upon receipt of the light-source turn-on instruction signal from the portable terminal, while causing the transmission/reception means to transmit the light-source turn-on reporting signal to the portable terminal. Accordingly, it is possible to turn on the light source at appropriate timing according to the photography by the camera.

When the light-source turn-off instruction signal is received, the light source control means turns off the light source, while causing the transmission/reception means to transmit the light-source turn-off reporting signal to the portable terminal. Accordingly, it is possible to turn off the light source at appropriate timing according to ending of the photography by the camera.

Meanwhile, the portable photography device of the present invention includes a portable terminal with camera and the lens module according to claim 7. The portable terminal includes: transmission/reception means on the terminal side that receives a light-source turn-on reporting signal and a light-source turn-off reporting signal from the transmission/reception means of the lens module, while transmitting a light-source turn-on instruction signal and a light-source turn-off instruction signal to the lens module; control means; and display control means. The control means carries out photography by the camera when receiving the light-source turn-on reporting signal from the lens module via the transmission/reception means and the transmission/reception means on the terminal side. When the photographing by the camera is ended, the control means transmits the light-source turn-off instruction signal to the lens module via the transmission/reception means on the terminal side and the transmission/reception means. When the light-source turn-off reporting signal is received from the lens module via the transmission/reception means and the transmission/reception means on the terminal side, the control means transmits the light-source turn-on instruction signal to the lens module via the transmission/reception means and the transmission/reception means on the terminal side. Thus, the control means associates the photographed image taken by the camera with the type of the light source and displays the photographed image on the screen of the portable terminal.

According to the present invention, the control means of the portable terminal carries out photography by the camera when the light-source turn-on reporting signal is received from the lens module via the transmission/reception means and the transmission/reception means on the terminal side. It is, therefore, possible to reliably photograph the object with the camera.

After the photography by the camera is ended, the light-source turn-off instruction signal is transmitted to the lens module via the transmission/reception means of the portable terminal and the transmission/reception means. It is possible, therefore, to reliably turn off the light source to prevent consumption of the battery.

The photographed image taken with the camera is associated with the type of the light source and displayed on the screen of the portable terminal by the display control means. Accordingly, the user can easily recognize the type of the photographed image displayed on the screen.

Advantageous Effects of Invention

According to the lens module of the present invention, it is possible to carry out multiple types of photography when photographing the object such as skin, while appropriately controlling turning on/off of the light source during shooting. According to the portable photography device of the present invention, it is possible to reliably carry out photography with the camera of the portable terminal when the light source is turned on.

DESCRIPTION OF EMBODIMENTS

Embodiments of the present invention will be described below by referring to the accompanying drawings.

First Embodiment

Figure 1:
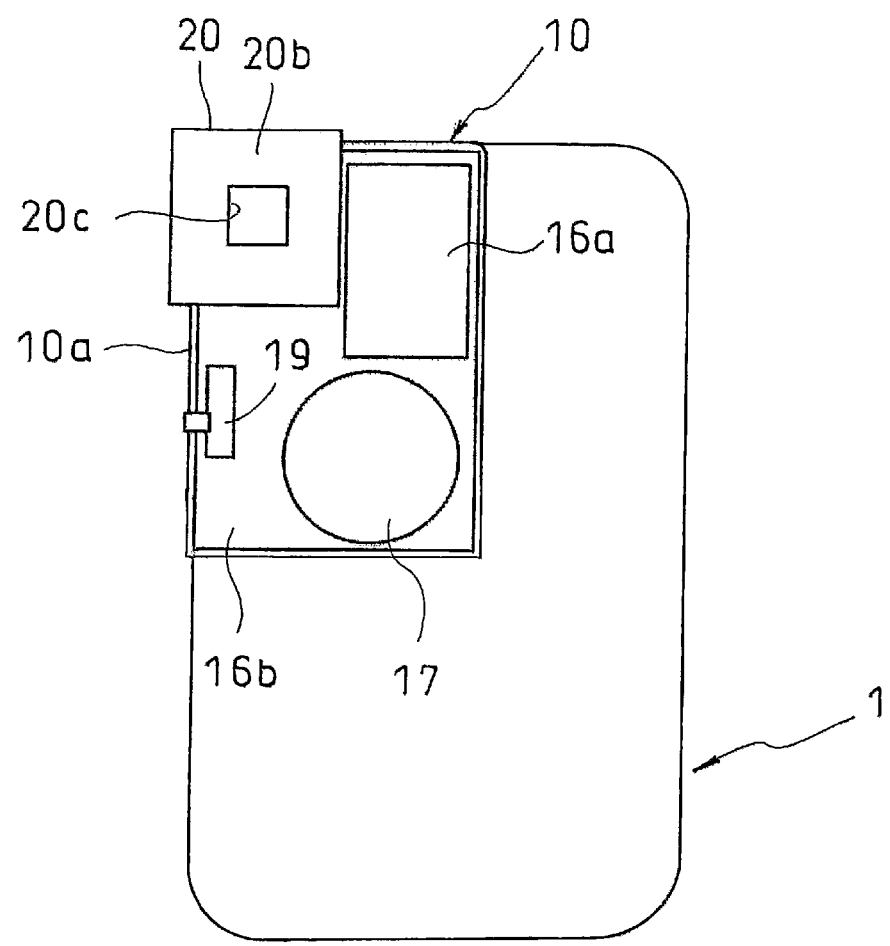
FIG. 1 is a front view illustrating a portable photography device according to a first embodiment of the present invention.
Figure 2:
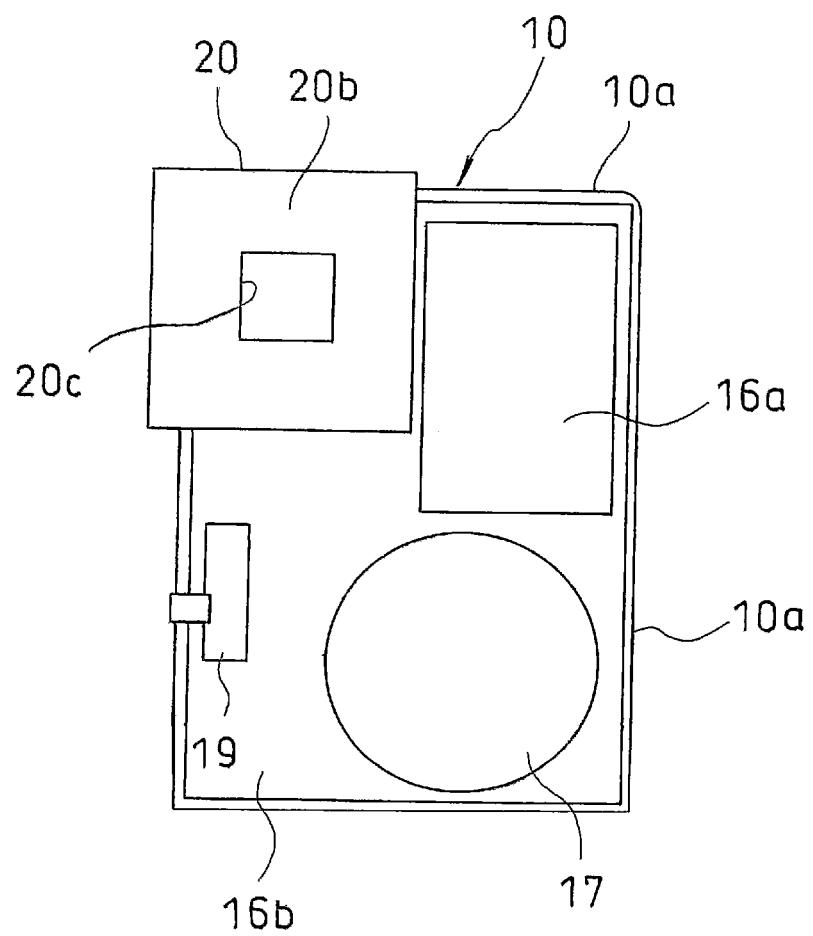
FIG. 2 is a front view illustrating a lens module of the above.

A portable photography device of the present embodiment, as illustrated in FIGS. 1 to 7B, includes a smartphone 1 (illustrated in FIGS. 1 to 7A) that is a portable electronic device (portable terminal) with a digital camera (a camera 2 including an image capturing device illustrated in FIG. 2), and a lens module 10 including a conversion lens 11 that includes two lenses 11a, 11b (illustrated in FIGS. 3 to 5, FIG. 7A) mounted on the camera 2 of the smartphone 1 to take a close-up photo of skin 24 (illustrated in FIG. 7A) in a magnified manner and LEDs 12, 13 (illustrated in FIGS. 3 to 7A) used for lighting during photography.

In FIGS. 1, 2, the lens module 10 is illustrated to disclose an internal circuit board 16b on which a battery 17, a power switch 19, an electronic circuit portion 16a are mounted. A front portion of the housing 10a other than a lens housing 20, which is described later, including a barrel 20a (illustrated in FIGS. 3 to 5) that supports the conversion lens 11 is not illustrated.

The lens module 10 includes the housing 10a. The housing 10a is a planar box-shaped housing other than the lens housing 20, and arranged to place the conversion lens 11 on a lens portion of the camera 2, which is located on the rear surface opposite to the front surface of the smartphone 1 on which a display (not illustrated) is provided.

The housing 10a is fixed on the smartphone 1 by clipping or banding. In the clipping, a clipping member (not illustrated) is provided on the lens module 10 to place the smartphone 1 between the clipping member and the lens module 10. That is, the smartphone 1 is placed between the lens module 10 and the clipping member fixed on the lens module 10 by elastic force.

In this case, the lens module 10 is movable in lateral and longitudinal directions within an allowed range relative to the rear surface of the smartphone 1 to correspond to various types of arrangements of the camera 2 of the smartphone 1.

In the banding, an elastic band (not illustrated), such as a rubber band, is installed on the lens module. Similar to a wrist band of a watch, the smartphone 1 is inserted into the internal side of the band to thereby install the lens module 10 on the smartphone 1. The conversion lens 11 is also movable in lateral and longitudinal directions relative to the rear surface of the smartphone 1.

The lens module 10 includes the conversion lens 11 described above, the LEDs 12, 13, an LED driving circuit 14 (illustrated in FIG. 7A) that drives the LED 12, and an LED driving circuit 15 (illustrated in FIG. 7) that drives the LED 13.

Figure 4:
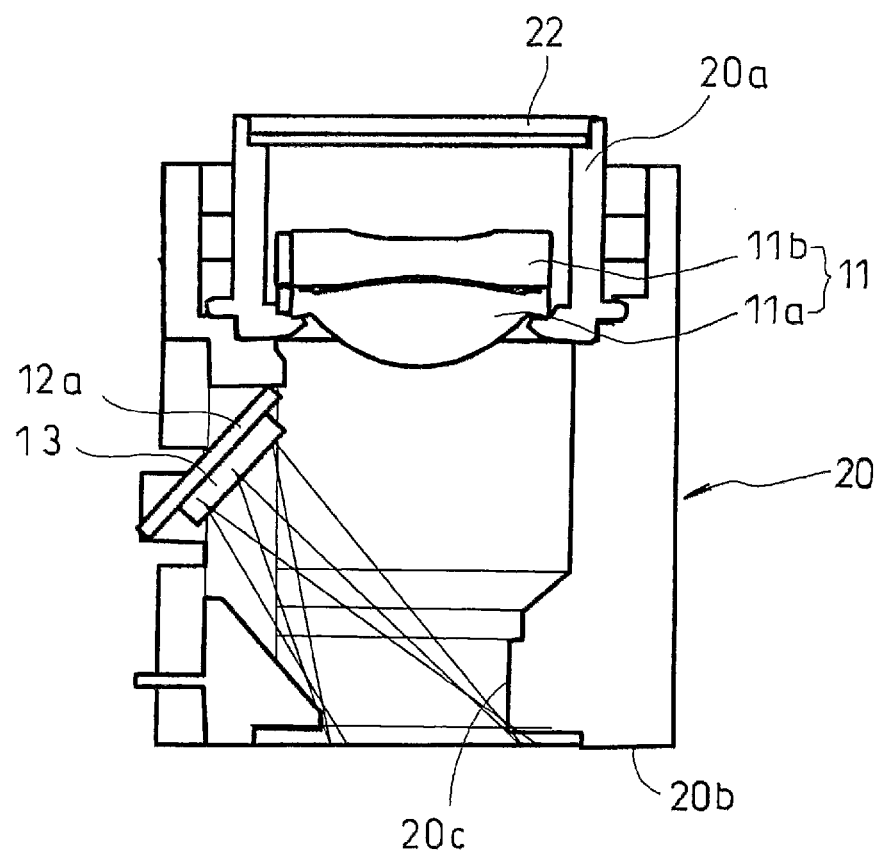
FIG. 4 is a cross-sectional view illustrating a lens housing portion of the lens module of the above.
Figure 5:
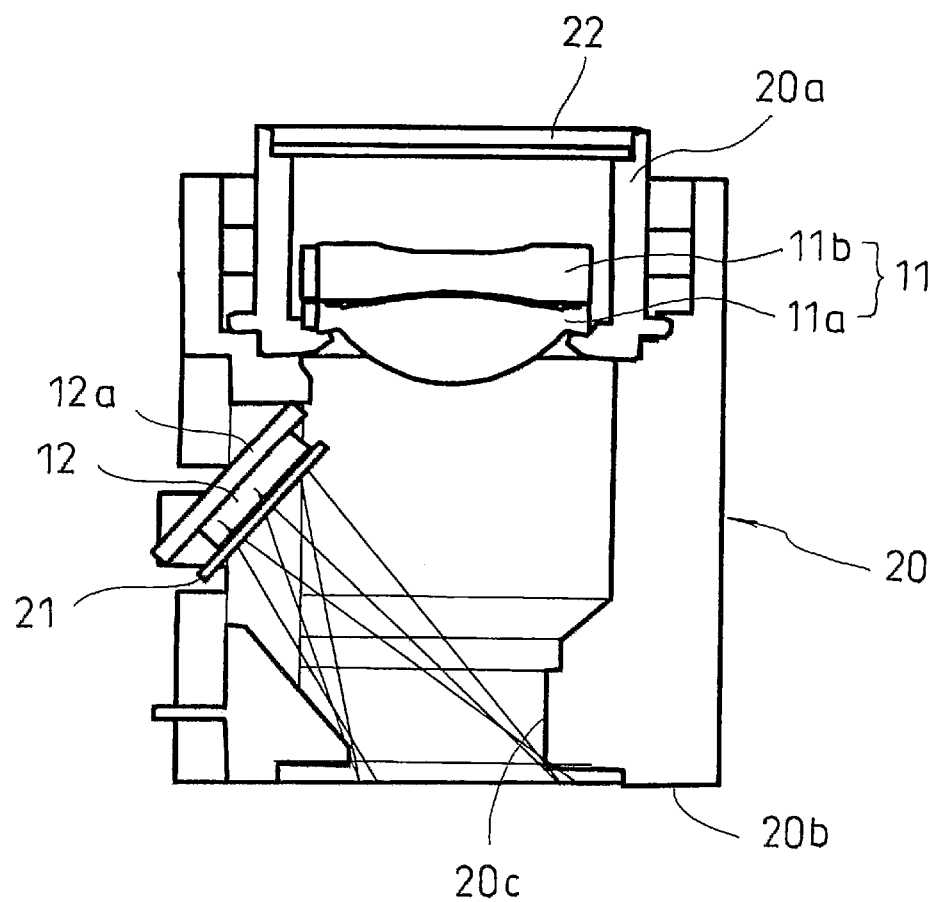
FIG. 5 is a cross-sectional view illustrating a lens housing portion of the lens module of the above.
Figure 6:
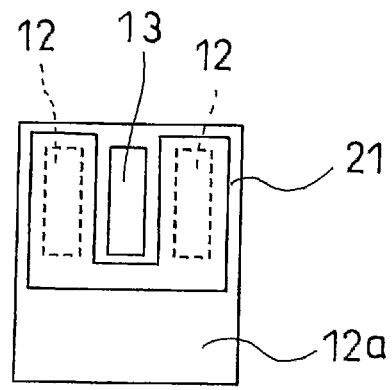
FIG. 6 is a plan view illustrating an LED substrate of the lens module of the above.

The lens module 10 also includes the lens housing 20 in which the conversion lens 11 is stored, as illustrated in FIGS. 4, 5. The lens housing 20 includes the barrel 20a that supports the conversion lens 11 on the base end side (the side to be mounted on the camera 2), with a tip end surface thereof being formed as an abutting portion 20b that abuts against skin 24 during photographing of the skin 24. The abutting portion 20b shields natural light when abutted against the skin 24. The abutting portion 20b is provided with a rectangular-shaped (generally square-shaped) opening 20c to allow photographing of a part of the skin 24 facing the opening 20c.

Figure 3:
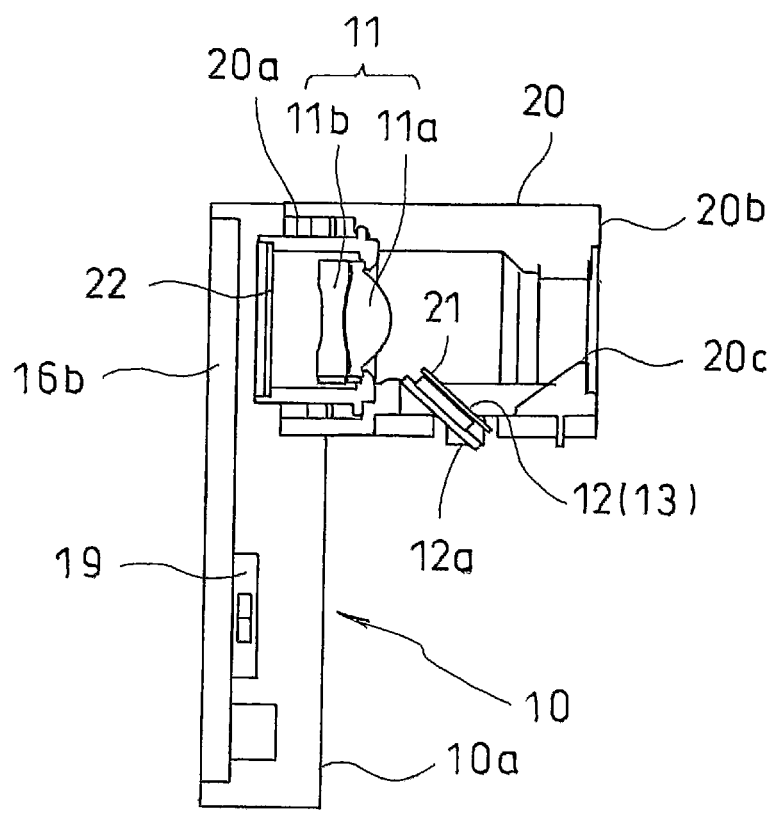
FIG. 3 is a cross-sectional view illustrating the lens module of the above.

As illustrated in FIGS. 3 to 5, the barrel 20a is fixed inside the base end portion (the end portion on the side to be mounted on the camera 2) of the lens housing 20, while supporting the conversion lens 11 including the lenses 11a and 11b. At the base end portion of the barrel 20a, a second polarizing plate 22 which is described later is also provided. Further, an LED substrate 12a (illustrated in FIGS. 3 to 6) including the LEDs 12, 13 to emit illuminating light for photography to the opening 20c of the abutting portion 20b is supported in the lens housing 20.

The LEDs 12, 13 are provided on the LED substrate 12a. Further, one LED 13 for photographing texture of the skin 24 and two LEDs 12 for photographing blots of the skin 24 are provided, which will be described later. The two LEDs 12 on the LED substrate 12a are covered by a first polarizing plate 21 which will be described later. The LED driving circuits 14, 15 are also provided on the LED substrate 12a. Alternatively, the LED driving circuits 14, 15 may be provided on the circuit board 16b.

As illustrated in FIGS. 3 to 5, the LED substrate 12a is arranged in such a manner that the LEDs 12, 13 directly illuminate the skin 24 facing the opening 20c of the lens housing 20. Alternatively, the LEDs 12, 13 may irradiate the skin 24 facing the opening 20c by reflecting the light on a half mirror.

The lens module 10 also includes a power supply circuit 18 (illustrated in FIG. 7A) and the power switch 19 on the circuit board 16b fixed on the housing 10a, the power supply circuit 18 including a battery 17 that supplies power to the LED driving circuits 14, 15, the CPU 16, and so on. A circular-shaped button battery is illustrated as the battery 17, but the battery such as an AAA battery may be used. The power switch 19 may be formed using various switches including a slide type switch, a push type switch, etc. It is not limited to place the power switch 19 at the housing portion of a lens 10 for the skin. Alternatively, a push type power switch may be provided at the abutting portion that abuts against the skin. The push type power switch may be switched on by bringing the push type power switch to abut against the skin. In this case, a contact member made of silicone rubber is urged on the outside to project from the abutting portion. The power switch is turned on when the contact member abuts against the skin, and the power switch is turned off when the contact member is detached. Alternatively, the power switch may be urged by more powerful force to turn on/off by pressing the power switch long by hand. In this case, the power switch is not turned on even when it is abutted against the skin.

The two LEDs 12, 13 emit slightly different colors of light. The LED 12 is used to photograph blots of the skin 24 and emits substantially white light. In contrast, the LED 13 is used to photograph the texture of the skin 24 and emits a near skin color light which includes more yellow component than the light emitting from the LED 12.

The first polarizing plate 21 is provided on the LED 12 for blot photographing, and the second polarizing plate 22 is provided between the conversion lens 11 and the camera 2. This is to photograph blots located slightly under the surface of the skin 24. These polarizing plates 21, 22 facilitate photographing of the blots by largely decreasing the reflection light on the surface of the skin 24, compared to the reflection light inside the skin 24 during photographing of the blots of the skin 24 with the LED 12. Polarizing directions of the first polarizing plate 21 and the second polarizing plate 22 are perpendicular to each other. The light of the LED 12 is passed through and polarized by the first polarizing plate 21. The polarized light is kept until after the reflection on the skin 24 such that it can hardly be passed through the second polarizing plate 22. Meanwhile, the light reflected inside the skin 24 is not polarized and is able to pass through the second polarizing plate 22. Alternatively, the polarizing plates 21, 22 may not be provided.

In such a lens module 10, the CPU 16 of the electronic circuit portion controls the LED 13 to emit light (turn on) when photographing the texture, while keeping the LED 12 to be turned off, and also controls the LED 12 to emit light when photographing blots, while keeping the LED 13 to be turned off.

As is well known, the smartphone 1 has a portable phone function to enable conversation using radio lines. The smartphone 1 also includes a display which is not illustrated and can connect to the Internet via radio lines. Thus, it is possible to transmit/receive e-mail via the Internet and view websites on a browser which is an application (APP). It is also possible to upload files to the server of a website or the like and download files from the server of a website or the like.

The smartphone 1 includes control means 3 (illustrated in FIG. 7A) including a CPU, ROM, RAM, etc., and can execute an APP as a program. A flash memory 4 is connected to the control means 3 as a storage apparatus capable of storing APPs (programs), such as downloaded APPs, music files, video files, or picture files.

The control means 3 can also control the camera 2 to photograph (capture images) and store the captured image data in the flash memory 4. It is also possible to analyze or process image data using an APP for image processing or image analysis.

The camera 2 includes the image capturing device to enable photographing still images and video images and, for example, photographs an image at a predetermined frame rate of 30 fps.

Further, the control means 3 includes light on/off detection means 3a that detects light on/off of the LEDs 12, 13, photography control means 3b that controls photography by the camera 2 when the light on/off detection means 3a has detected the on/off state of the LEDs 12, 13, and display control means 3c that associates the photographed image taken by the camera 2 according to the control by the photography control means 3b with the LEDs 12, 13 and displays the photographed image on the screen of the portable terminal.

The lens (lens module) 10 for the skin includes the conversion lens 11 with the LEDs 12, 13, the LED driving circuit 14 that drives the LED 12, and the LED driving circuit 15 that drives the LED 13. The lens module 10 also includes the CPU 16 that controls the on/off state of the LEDs 12, 13 as the light source control means via the LED driving circuits 14, 15. The CPU 16 is actually not formed by the CPU alone and is formed as an one-chip microcomputer (IC chip) that includes a storage apparatus such as the ROM or the RAM.

The lens (lens module) 10 for the skin also includes the LED driving circuits 14, 15, the power supply circuit 18 including the battery 17 that supplies power to the LED driving circuits 14, 15, the CPU 16, etc., and the power switch 19.

The lens (lens module) 10 for the skin includes a lens barrel 20 of the conversion lens 11. The lens barrel 20 also functions as a hood, while supporting the conversion lens 11, to shield the natural light with the tip end surface being in contact with the skin.

Example 1

Figure 8:
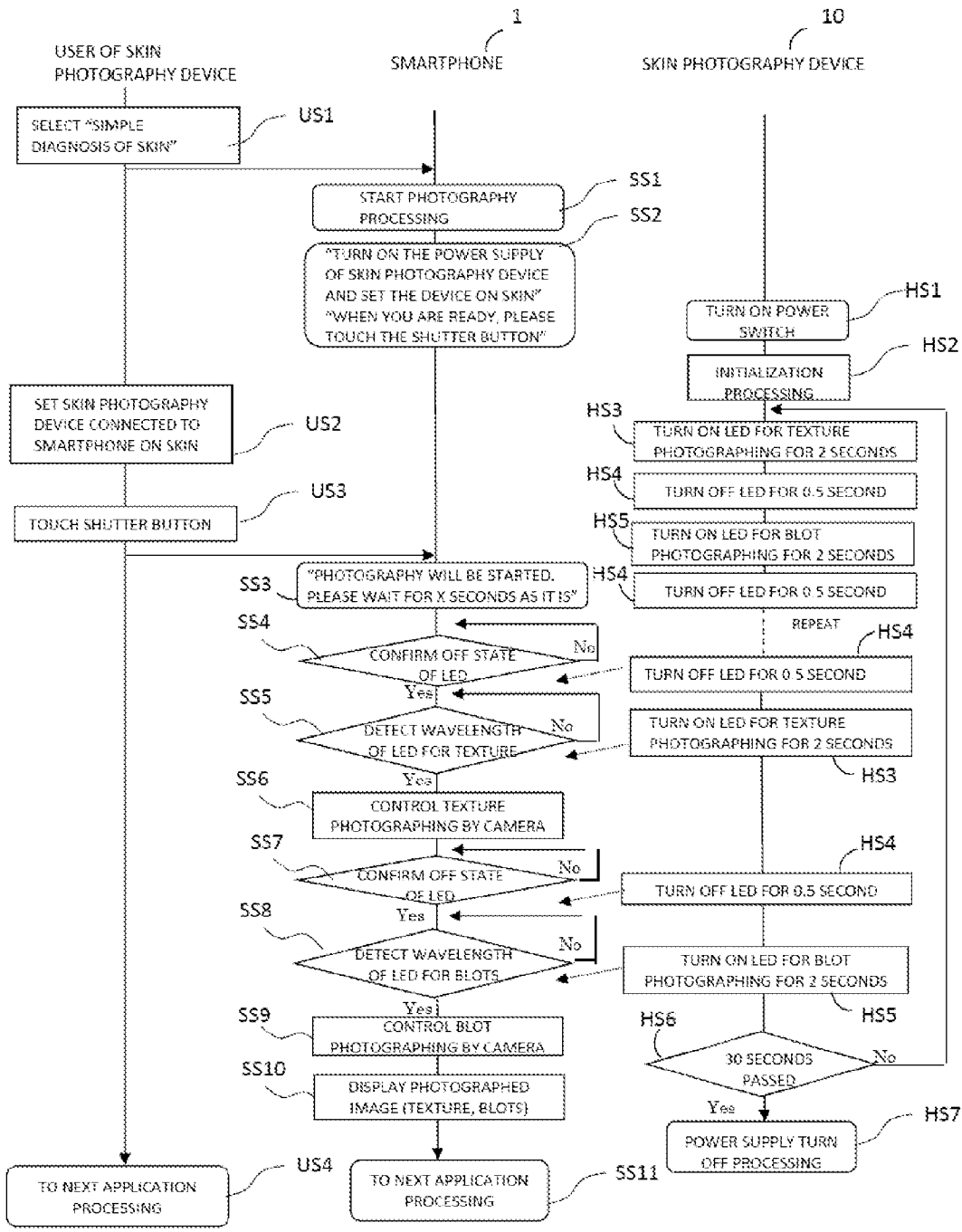
FIG. 8 is a flowchart of Example 1 for explaining an example of a method of photographing skin of a face of a person with a portable photography device according to the first embodiment of the present invention.

In Example 1, a first example of a method of photographing skin of a face of a person with a portable photography device of a first embodiment will be described by referring to FIG. 8.

First, a user of skin photography device (user) turns on the power supply of the smartphone 1 and selects a "simple diagnosis of skin" application on the screen (step US1).

Accordingly, photographing processing of the smartphone 1 is started (step SS1). On the screen of the smartphone 1, a message saying "Turn on the power supply of the skin photography device and set the device on the skin. Touch the shutter button when you are ready." is displayed (step SS2). This message may be a voice message and can be used together with a written message.

In the lens 10 for the skin, when the power switch is turned on (step HS1), the lens 10 is subjected to initialization processing (step HS2) and an LED blinking mode is started. That is, the CPU (light source control means) 16 successively and repeatedly carries out control of the two types of LEDs 12, 13 to turn on/off at predetermined time intervals.

First, the LED 13 for texture photographing is turned on for two seconds (step HS3), followed by turning off of the LED 13 for 0.5 second (step HS4). Next, the LED 12 for blot photographing is turned on for two seconds (step HS5), and the LED 12 is then turned off for 0.5 second (step HS4).

Subsequently, the steps HS3 to HS5 are repeated successively, and when 30 seconds has passed (step HS6) after the initialization processing (step HS2), the CPU 16 turns off the power supply (step HS7). If 30 seconds has not been passed in step HS6, then steps HS3 to HS5 are successively repeated until 30 seconds has passed (step HS6) and the CPU 16 then turns off the CPU 16 (step HS7).

Thus, in the lens 10 for the skin, the LEDs 13, 12 are successively turned on/off repeatedly at predetermined time intervals (turning on for 2 seconds and turning off for 0.5 second).

When the battery 17 of the lens (lens module) 10 for the skin is consumed, at least one of the LEDs 12, 13 is made to blink at predetermined time intervals (e.g., intervals of 0.2 second) for a predetermined time period (e.g., 3 seconds) before 30 seconds has passed in step HS6 and the power supply is turned off in step HS7 to thereby report to the user of the consumption of the battery. In this case, the above blinking processing should be preset in the LED driving circuits 14, 15 and, when the CPU 16 of the lens 10 for the skin detects the consumption of the battery 17 via the power supply circuit 18, the LED driving circuits 14, 15 are instructed to blink the LEDs 12, 13 as above. With this structure, the consumption of the battery 17 can be reliably reported without requiring a special display function to notify the user of the consumption of the battery 17.

In this case, power supply voltage monitoring means, such as a battery voltage drop detecting circuit, is provided in the power supply circuit 18, by including a signal outputting function to output a signal when the voltage of the battery 17 becomes equal to or smaller than a preset reference voltage.

When the consumption of the battery 17 has progressed, the LEDs 12, 13 start blinking to cause a rapid voltage drop. Accordingly, the battery voltage drop detecting circuit provided in the power supply circuit 18 is activated before 30 seconds have passed in step HS6 to possibly stop the blinking operation of the LED according to the instruction by the CPU 16. To prevent the blinking of the LED from being ended earlier than a fixed time period (30 seconds) when the battery 17 has been consumed, the following processing will be carried out. Specifically, if the CPU 16 detects a voltage drop of the battery via the battery voltage drop detecting circuit at least once in the 30 seconds in step HS6, such information is recorded as flag information in non-volatile memory, which is not illustrated, provided in the lens 10 for the skin.

With such flag information, the CPU 16 instructs the LED driving circuits 14, 15 not to turn on the LEDs 12, 13 for photographing the skin next time the power switch 19 is pressed. When the battery 17 is replaced by new one and the battery voltage of, for example, at least 4.3 V is detected, the flag recorded in the non-volatile memory is cleared (deleted) from the volatile memory.

Similarly, such a user reporting function to report the consumption of the battery 17 and a blinking preventing function to prevent blinking of the LED of less than the fixed time period (30 seconds) while the battery 17 is consumed can be carried out in Examples 2 to 8 which will be described later.

During the blinking mode of the LED in the lens for the skin, a user of skin photography device sets the skin photography device connected to the smartphone on the skin (step US2) and touches the shutter button displayed on the screen of the smartphone (step US3).

Figure 7A:
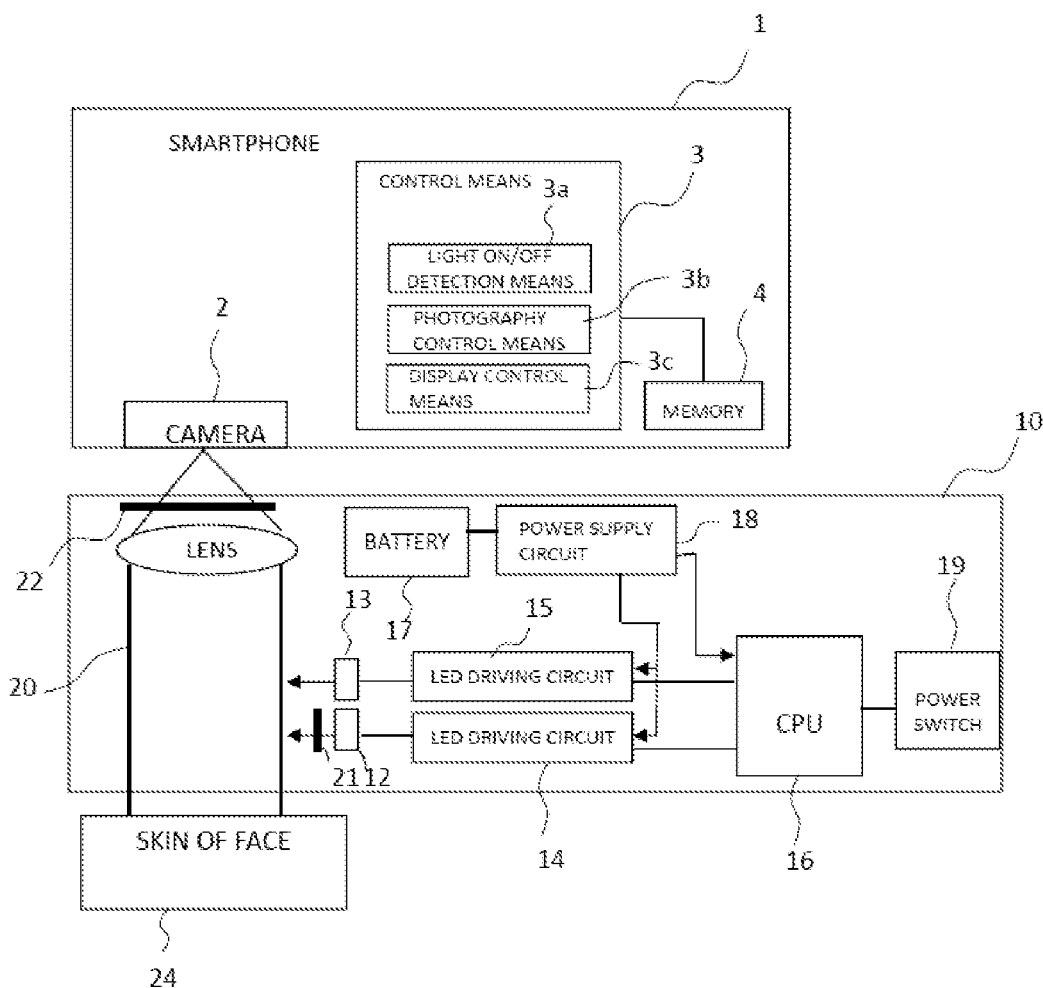
FIG. 7A is a block diagram of the above.
Figure 7B:
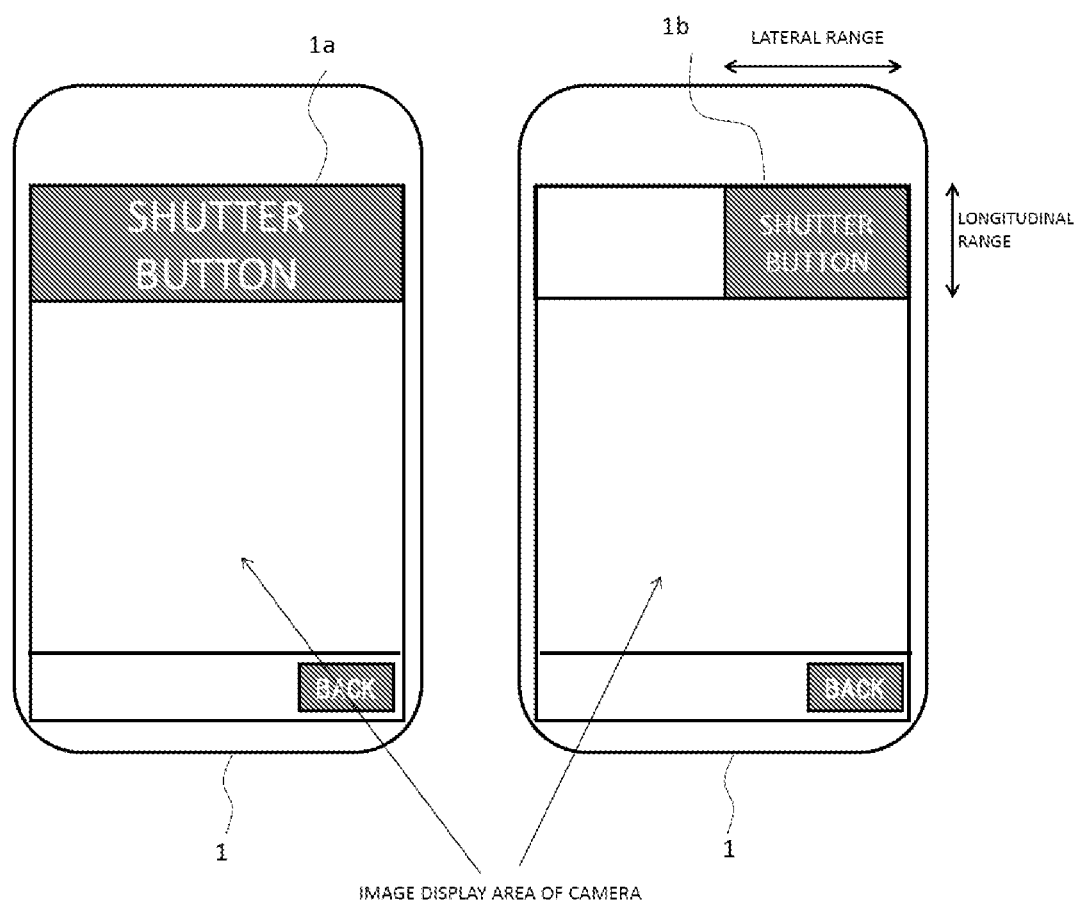
FIG. 7B are front view of a smartphone of the above, in which (a) illustrates a shutter button arranged on the upper end of the screen and (b) illustrates the shutter button arranged on the generally right half of the upper end.

The user can hardly see the screen during the photographing operation. The shutter button, therefore, is provided such that the user can touch the shutter button without seeing the screen, and an erroneous operation by the user to touch other buttons on the screen can be prevented. Specifically, as illustrated in FIG. 7B(a), a shutter button 1a is displayed on the upper part of the screen by assuming that the shutter button 1a is touched by an index finger while the smartphone 1 is held by hand. The shutter button 1a is preferably disposed within ⅕ to ⅓ of the longitudinal size of the screen from the upper end of the screen.

For users who use right hands during the operation, the shutter button 1b may preferably be disposed in the right half of the above range of the screen and preferably within ¼ to ½ to the left from the right end of the screen, as illustrated in FIG. 7B(b). For users who use left hands during the operation, the shutter button 1b may preferably be disposed at a symmetrical location relative to the position described above. This method is effective when it is assumed that the user operates while seeing the photographing screen using a hand mirror.

It is also necessary to arrange a cancellation button to cancel photography on the screen, but such a button needs to be disposed at a place where the user most hardly touches erroneously during photographing. It is preferable to dispose such a button at a position in the lower half of the screen or at ⅓ of the longitudinal screen size from the bottom end of the screen, by considering that the user may touch the shutter button by the index finger while holding the smartphone by abutting it against the skin. During cancellation, as the user usually carries out the operation by seeing the screen, it is preferable also visually to arrange the button at ⅕ of the longitudinal screen size from the lower end of the screen.

When the user touches the shutter button, the voice message saying "Photography will be started. Do not move and wait for 5 seconds as it is." is provided to the user (step SS3).

In the smartphone 1, a standby state is entered, following step SS3, until the light on/off detection means 3a confirms the off state of the LEDs 12, 13 (step SS4). After the confirmation of the off state of the LEDs 12, 13 in step SS4, the light on/off detection means 3a detects the on state of the LED 13 for texture photographing by detecting the wavelength of light of the LED 13 (step SS5). Subsequently, the photography control means 3b controls photography by the camera 2 at appropriate time during the on state by considering the lighting time (2 seconds) of the LED 13 (step SS6). That is, the shutter sound of the camera 2 is generated to capture a still image. By doing this, a photographed image for the texture can be obtained.

The standby state is then entered until the light on/off detection means 3a confirms the off state of the LEDs 12, 13 (step SS7). Upon confirmation of the off state, the light on/off detection means 3a detects the on state of the LED 12 for blot photographing by detecting the wavelength of light of the LED 12 (step SS8). Subsequently, the photography control means 3b controls the photography by the camera 2 at appropriate time during the on state by considering the lighting time (2 seconds) of the LED 12 (step SS9). That is, the shutter sound of the camera 2 is generated to capture a still image. By doing this, a photographed image for the blots can be obtained.

Next, the display control means 3c associates the two types of photographed images taken by the camera 2 for the texture and the blots with the LEDs 13, 12, respectively, and displays such images on the screen of the smartphone 1 (step SS10). Specifically, the images are displayed by determining whether the photographed image is the image for the texture taken using the LED 13 as the light source, or the image for the blots taken using the LED 12 as the light source.

The image photographed by the camera 2 in step SS6 is the image for the texture, and the image photographed by the camera 2 in step SS8 is the image for the blots. These images photographed by the camera 2 are stored in the memory 4 as the image for the texture and also stored in the memory 4 as the image for the blots. By reading the individual image from the memory 4, it is therefore possible to display the photographed image for the texture and the photographed image for the blots on the screen of the smartphone 1.

When the display is ended, the user selects ending the photography processing of the smartphone 1, restarting the photography, or selecting the next application processing by the user of skin photography device. The flowchart of FIG. 8 illustrates the case when the user of skin photography device selects the next application processing (US4) and the process proceeds to the next application processing (step SS11).

In this example, the blots are photographed after photographing the texture, but the photographing order may be reversed.

There are various types of smartphones 1, such that the detection of the wavelength of the LED and the time of control processing of the photographing camera would be different depending on the type. By considering the type that takes the longest time, the lighting time of the LED is set to 2 seconds in this example, but it would substantially be no problem if the time is set to about 1 second.

Thus, the lighting time of the LED has been set to 2 seconds in the present embodiment, but the necessary time for lighting changes depending on the performance of the smartphone 1. If it takes relatively long time for focus adjustment of the camera 2 of the smartphone 1, it is necessary to set long lighting time of the LED. In contrast, however, if the smartphone 1 can quickly carry out the focus adjustment, such long lighting time of the LED may cause a problem of extending the standby time.

Accordingly, a lighting time changing function to change the lighting time of the LED may be added. For example, several lighting time periods (e.g., 1.5 seconds, 2.0 seconds, 2.5 seconds, and 3.0 seconds, etc.) may be preset in the LED driving circuits 14, 15 of the lens module 10. When the power switch 19 is pressed long (e.g., for 5 seconds), the CPU 16 should detect the long pressing and instruct the LED driving circuits 14, 15 to successively change (switch) the lighting time of the LED (e.g., in order of 1.5 seconds, 2.0 seconds, 2.5 seconds, and 3.0 seconds).

In this structure, it is possible to change the lighting time of the LED each time the power switch 19 is pressed long to thereby set an appropriate lighting time of the LED according to the performance (focusing performance) of the camera of the smartphone 1.

Such an LED lighting time changing function may be added similarly to Examples 2 to 8 which will be described later.

When the lighting time of the LED is changed, it is necessary to report the change to the user. The reporting may be carried out by providing an LED capable of emitting multiple types of light in the power switch 19 and associating the multiple colors of illumination of the LED with multiple lighting time periods. The color of the illumination of the LED is changed each time the power switch 19 is pressed long.

Alternatively, several types of the LEDs may be provided at appropriate portions of the lens module 10 according to the lighting time period of the LED to turn on the LED that corresponds to the lighting time of the LED each time the power switch 19 is pressed long.

If the wavelength of the LED 12 for blot photographing is not detected following the detection of the wavelength of the LED 13 for texture photographing, which is not illustrated, there is a possibility that the natural light has been accidentally identified as the LED 13 for texture photographing during the detection of the wavelength of the LED 13 for texture photographing. In this case, the processing needs to be redone.

According to this example, when the light source control means (CPU) 16 controls the light sources of LEDs 13, 12 to successively repeat turning on and turning off the LEDs 13, 12 at predetermined time intervals, if the light on/off detection means 3a detects the on state of each of the LEDs 12, 13, the photography control means 3b lets the camera 2 to carry out photography. In contrast, if the off state of the LEDs 12, 13 is detected, the light on/off detection means 3a holds the photography by the camera to standby until the light on/off detection means detects the wavelength of the LED 12 or the LED 13. As a result, both texture and blot photographing of the skin can be reliably carried out with the camera 2.

Further, the photographed image taken by the camera 2 is associated with the LED 12 or the LED 13 and displayed on the screen of the smartphone 1 by the display control means 3c, such that the user can easily confirm the type of the photographed image displayed on the screen. That is, the user can easily confirm whether the image is the photographed image for the texture or the photographed image for the blots.

Example 2

In Example 1 described above, the texture is photographed first by the camera 2 by detecting the wavelength of the LED 13 for texture photographing and, after the off state of the LEDs 13, 12 is confirmed, the wavelength of the LED 12 for blot photographing is detected.

Figure 9:
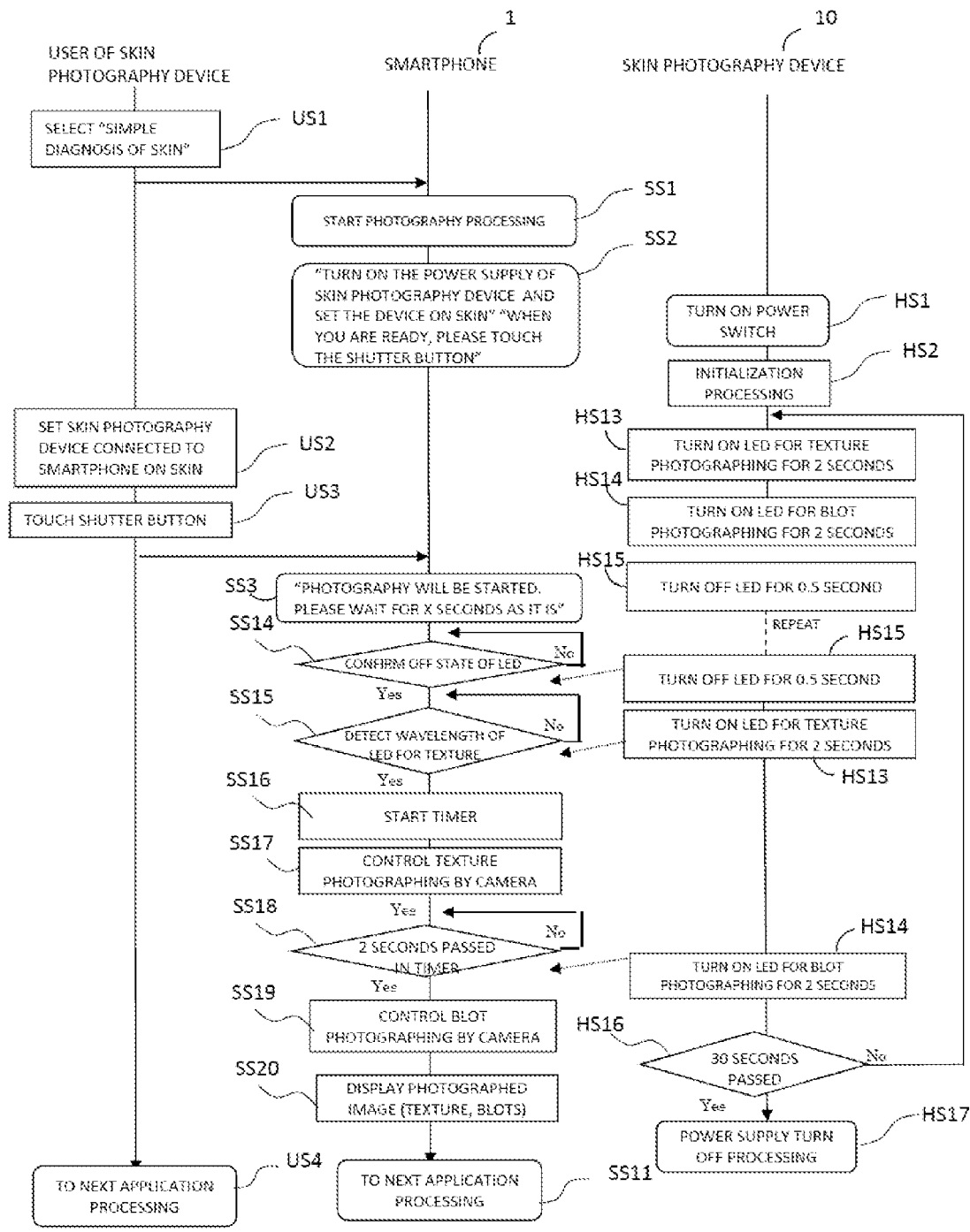
FIG. 9 is a flowchart of Example 2 for explaining an example of the above.

An advantage of this system is an ability to use either type of lens for the skin without changing the software on the smartphone 1 side, even when the time to detect the LED wavelength and the photography control time of the camera become shorter as a result of improved performance or the like of the smartphone 1, and a new type of the lens for the skin having a shorter lighting time of the LED 12 for blot photographing and the LED 13 for texture photographing than 2 seconds on the lens 10 side is introduced. Meanwhile, if the lighting time of 2 seconds of the LED 12 for blot photographing and the LED 13 for texture photographing is not going to be changed in the future, turning off the LEDs 12, 13 for 0.5 second after the on state of the LED 13 may be omitted on the condition that the lighting time of 2 seconds of the LED 13 for texture photographing is not changed. A control sequence of this case will be described below. That is, in Example 2, a second example of the method of photographing skin of a face of a person with a portable photography device of the first embodiment will be described by referring to FIG. 9.

In this example, steps US1 to US4 and steps SS1 to SS3 are similar to those in Example 1 and the description thereof will not be repeated.

In the lens 10 for the skin, the CPU (light source control means) 16 repeatedly controls, after the initialization processing, the two types of LEDs 13, 12 to turn on the LEDs 13, 12 successively for a predetermined time period (2 seconds), and after having turned on the LEDs 13, 12, turn off the LEDs 13, 12 for a predetermined time period (0.5 second).

Specifically, the CPU 16 first turns on the LED 13 for texture photographing for 2 seconds (step HS13), and then turns on the LED 12 for blot photographing for 2 seconds while turning off the LED 13 (step HS14). As the LED 12 is turned on simultaneously with turning off of the LED 13, both LEDs 13, 12 are not turned off simultaneously while the LEDs 13, 12 are turned on/off. After that, the LEDs 13, 12 are turned off for 0.5 second (step HS15).

Steps HS13 to HS15 are carried out successively and repeatedly and, when 30 seconds has passed (step HS16) after the initialization processing (step HS2), the CPU 16 turns off the power supply (step HS17). If 30 seconds has not been passed in step HS16, then steps HS13 to HS15 are carried out successively and repeatedly until 30 seconds has passed (step HS16), and then the CPU 16 turns off the power supply (step HS17).

Thus, in the lens 10 for the skin, the control is carried out repeatedly to turn on the LEDs 13, 12 successively for the predetermined time period (2 seconds) and, after having turned on the LEDs 13, 12, turn off the LEDs 13, 12 for the predetermined time period (0.5 second).

In the smartphone 1, the light on/off detection means 3a enters the standby state after step SS3 until the off state of the LEDs 12, 13 is confirmed (step SS14). Upon confirmation of the off state of the LEDs 12, 13 in step SS14, the light on/off detection means 3a detects the on state of the LED 13 for texture photographing by detecting the wavelength of light of the LED 13 (step SS15).

Then a timer is started (step SS16). The timer is installed in the smartphone 1 as a clock function to allow the control means 3 to carry out ON/OFF control of the timer and detect elapsed time in the timer.

After the timer is started, the photography control means 3b controls photography by the camera 2 (step SS17). That is, the shutter sound of the camera 2 is generated to capture a still image. Since the on state of the LED 13 for texture photographing has been confirmed in step SS15, it is possible to obtain a photographed image for the texture.

Next, the LED 13 for texture photographing is lighted for 2 seconds and, when the control means 3 detects that 2 seconds has passed with the timer (step SS18), the photography control means 3b carries out the photography control of the camera 2 (step SS19). That is, the shutter sound of the camera 2 is generated to capture a still image. Since the on state of the LED 13 for texture photographing is confirmed in step SS15 and 2 seconds has passed after turning on, the LED 12 for blot photographing is being turned on in step SS19. As a result, the photographed image for the blots can be obtained.

The photography control means 3b thus carries out photography control of the camera at predetermined time intervals (2 seconds) in synchronization with turning on of the LEDs 13, 12, the photographed images for the texture and the blots can be obtained.

Next, the display control means 3c associates the two types of photographed images for the texture and the blots, which have been photographed by the camera 2, with the LEDs 13, 12 and displays the images on the screen of the smartphone 1 (step SS20). Specifically, the images are displayed by determining whether the photographed image is the image for the texture taken using the LED 13 as the light source, or the image for the blots taken using the LED 12 as the light source. Since the image photographed by the camera 2 in step SS17 is the image for the texture and the image photographed by the camera 2 in step SS19 is the image for the blots, the individual images photographed by the camera 2 are stored in the memory 4 as the image for the texture and also stored in the memory 4 as the image for the blots. By reading the individual image from the memory 4, it is therefore possible to display the photographed image for the texture and the photographed image for the blots on the screen of the smartphone 1.

When the display is ended, the user selects ending the photography processing of the smartphone 1, restarting the photography, or selecting the next application processing by the user of skin photography device. In the case of the flowchart of FIG. 9, it is illustrated that the user of skin photography device selects the next application processing (US4) and the process moves to the next application (step SS11).

In this example, the blots are photographed after photographing the texture, but the photographing order may be reversed.

According to this example, the CPU (light source control means) 16 repeatedly controls the two types of LEDs 13, 12 to successively turn on the LEDs 13, 12 for the predetermined time period and, after having turned on the LEDs 13, 12, turn off the LEDs 13, 12 for the predetermined time period (0.5 second). In this state, when the light on/off detection means 3a detects the lighting of the LED 13 first time after the off state of the LEDs 13, 12 is detected, the photography control means 3b controls photography by the camera 2. The photography control means 3b then controls the photography by the camera 2 at the predetermined time intervals (2 seconds) by the timer in synchronization with turning on of the LED 12. It is possible, therefore, to reliably carry out photography by the camera 2 of the smartphone 1 by using the two types of LEDs 13, 12. In addition, there is an advantage that the photography using the two types of LEDs 13, 12 can be carried out only by detecting the off state of the LEDs 13, 12 and, after the off state, detecting the first lighting of the LED 13 by the light on/off detection means 3a.

In addition, the user can easily confirm the type of the photographed image displayed on the screen of the smartphone 1, as in Example 1, as the photographed image taken by the camera 2 is associated with the LED 13 or the LED 12 and displayed on the screen of the smartphone 1 by the display control means 3c. That is, the user can easily confirm whether the image is the photographed image for the texture or the photographed image for the blots.

Example 3

In Examples 1 and 2 described above, the photography by the camera is started after having waited for the detection of the wavelength of the LED 13 for texture photographing. When the shutter button is touched immediately after the start of the on state of the LED 13 for texture photographing, the photography by the camera is started next time the LED 13 for texture photographing is turned on after the LED 13 for texture photographing is turned off and the LED 12 for blot photographing is turned on and off. To prevent variation of time until the start of photography caused by different timing of touching the shutter button, it would be better to carry out the photography after determining whether the wavelength of the LED is for texture photographing or blot photographing. In this case, it takes longer for carrying out the processing than simply determining whether the LED 13 for texture photographing or the LED 12 for blot photographing is on. It would be safer, therefore, to set the lighting time of the LEDs 12, 13 longer than that in Examples 1 and 2. In Example 3, the lighting time is set to 2.2 seconds. The control sequence of this case will be described by referring to FIG. 10.

In this example, steps US1 to US4, steps SS1 to SS3, and steps HS1 to HS7 are similar to those in Example 1 and the description thereof will not be repeated. This example differs from Example 1 in that the lighting time of the LED 13 for texture photographing is set to 2.2 seconds in step HS3, and the lighting time of the LED 12 for blot photographing is set to 2.2 seconds in step HS5.

Figure 10:
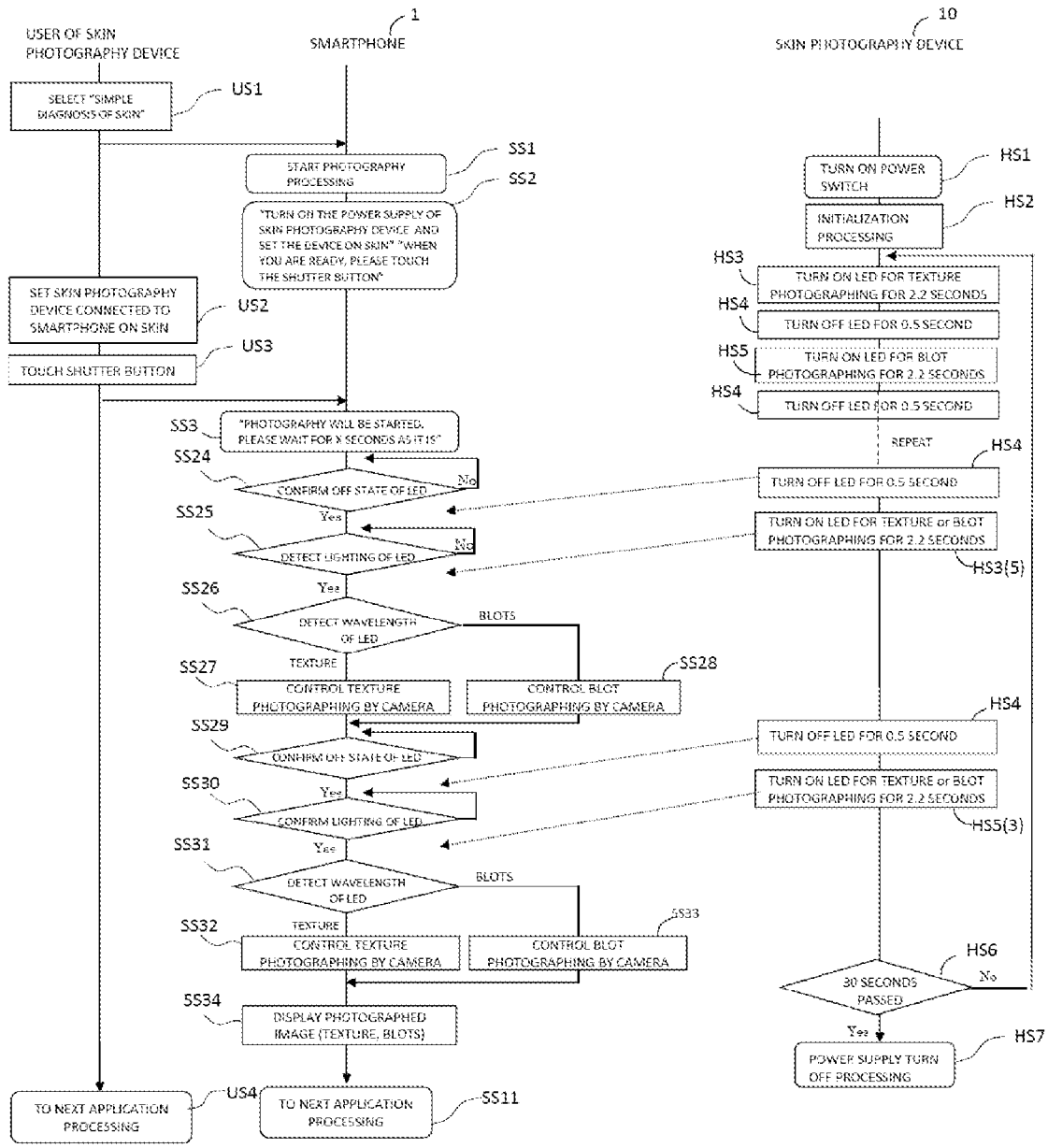
FIG. 10 is a flowchart of Example 3 for explaining an example of the above.

In the lens 10 for the skin, the control is carried out repeatedly to turn on the LEDs 13, 12 successively for the predetermined time period (2.2 seconds) and, after the LED 13, 12 is turned off, turn off the LEDs 13, 12 for the predetermined time period (0.5 second). Since which LED (LED 12 or 13) is turned on after the LEDs 12, 13 are turned off is not known, the smartphone 1 identifies the wavelength of the LED to determine which LED (LED 13 or LED 12) has been turned on (steps SS26 and SS31). In FIG. 10, a step of "photographing the texture or blots and turning on the LED for 2.2 seconds" is indicated by step HS3(5), while a step of "photographing the blots or texture and turning on the LED for 2.2 seconds" is indicated by step HS5(3).

In the smartphone 1, the light on/off detection means 3a enters the standby state after step SS3 until the off state of the LEDs 12, 13 is confirmed (step SS24). After the confirmation of the off state of the LEDs 12, 13 in step SS24, the light on/off detection means 3a detects the lighting of the LED 12 or LED 13 (step SS25) and identifies the wavelength of the LED 12 or LED 13 (step SS26), in order to determine whether the LED which is being turned on is the LED 12 for blot photographing or the LED 13 for texture photographing.

If the LED being turned on is the LED 13 for texture photographing, the photography control means 3b controls the photography by the camera 2 (step SS27). That is, the shutter sound of the camera 2 is generated to capture a still image. By doing this, the photographed image for the texture can be obtained.

Meanwhile, if the LED being turned on is the LED 12 for blot photographing, the photography control means 3b controls the photography by the camera 2 (step SS28). That is, the shutter sound of the camera 2 is generated to capture a still image. By doing this, the photographed image for the blots can be obtained.

Next, the standby state is entered until the light on/off detection means 3a confirms the off state of the LEDs 12, 13 (step SS29). The light on/off detection means 3a then detects the on state of the LEDs 12, 13 (step SS30) as in step SS25, and identifies the wavelength of the LEDs 12, 13 (step SS31) as in step SS26, to determine whether the LED being turned on is the LED 12 for blot photographing or the LED 13 for texture photographing.

If the LED being turned on is the LED 13 for texture photographing, the photography control means 3*b* controls the photography by the camera 2 (step SS32). That is, the shutter sound of the camera 2 is generated to capture a still image. By doing this, the photographed image for the texture can be obtained.

Meanwhile, if the LED being turned on is the LED 12 for blot photographing, the photography control means 3*b* controls the photography by the camera 2 (step SS33). That is, the shutter sound of the camera 2 is generated to capture a still image. By doing this, the photographed image for the blots can be obtained.

As described above, the photography is carried out two times each for the texture photographing and the blot photographing.

Next, the display control means 3*c* associates the two types of photographed images for the texture and the blots, which have been photographed by the camera 2, with the LEDs 13, 12 and displays the images on the screen of the smartphone 1 (step SS34). Specifically, the images are displayed by determining whether the photographed image is the image for the texture taken using the LED 13 as the light source, or the image for the blots taken using the LED 12 as the light source.

When the display is ended, the user selects ending the photography processing of the smartphone 1, restarting the photography, or selecting the next application processing by the user of skin photography device. In the flowchart of FIG. 10 illustrates the case where the user of skin photography device selects the next application processing (US4) and the process proceeds to the next application processing (step SS11).

According to this example, a similar effect as in Example 1 can be obtained, and an advantage of preventing variation of time before the start of photography due to different timing of touching the shutter button can also be obtained.

Example 4

In Examples 1 to 3, the LEDs having small deviation from the prescribed values should be installed on the lens 10 for the skin as the LEDs 13, 12 for texture photographing and blot photographing, in order to prevent erroneous identification of the wavelength of the LED 12 for blot photographing or the wavelength of the LED 13 for texture photographing on the side of the smartphone 1. However, actual wavelengths of the LEDs fluctuate, and the LEDs having wavelengths closer to the prescribed values are selected and used. This causes a cost increase of the LEDs. In Example 4 below, it is described that the allowable deviation value from the prescribed value is increased in order to decrease the cost of the LEDs. To achieve this, both LEDs 13, 12 should be compared relatively with each other, instead of identifying the wavelength components of the LEDs based on absolute values, to thereby identify the LED having a wavelength component closer to red as the LED 13 for texture photographing and the LED having a wavelength component closer to blue as the LED 12 for blot photographing. The control sequence of this case will be described by referring to FIG. 11.

In this example, steps US1 to US4, steps SS1 to SS3, and steps HS1 to HS7 are similar to those in Example 3 and the description therefor will not be repeated.

In the smartphone 1, a standby state is entered, following step SS3, until the light on/off detection means 3*a* confirms the off state of the LEDs 12, 13 (step SS4). After the confirmation of the LEDs 12, 23 in step SS4, the light on/off detection means 3*a* detects the lighting of either the LED 12 or LED 13 (step SS40). In step SS40, the light on/off detection means 3*a* only detects the lighting of the LEDs and does not identify whether the LED is the LED 13 for texture photographing or the LED 12 for blot photographing.

Upon detection of the lighting of the LED, the photography control means 3*b* controls the photography by the camera 2 (SS41). That is, the shutter sound of the camera 2 is generated to capture a still image. By doing this, a photographed image for the texture or for the blots can be obtained.

Subsequently, the standby state is entered until the light on/off detection means 3*a* confirms the off state of the LEDs 12, 13 (step SS42). Upon confirmation of the off state, the light on/off detection means 3*a* detects the lighting of the LED 12 or the LED 13 (step SS43). The light on/off detection means 3*a* only detects the lighting of the LEDs and does not identify the LED as the LED 13 for texture photographing or the LED 12 for blot photographing. In step SS43, however, if the LED 13 for texture photographing is on in step 40, the LED 12 for blot photographing comes to be turned on in step SS43. In contrast, if the LED 12 for blot photographing is lighting in step 40, the LED 13 for texture photographing comes to be turned on.

Upon detecting the lighting of the LED, the photography control means 3*b* carries out the photography control of the camera 2 (step SS44). That is, the shutter sound of the camera 2 is generated to capture a still image. By doing this, a photographed image for the texture or for the blots can be obtained. In step SS44, the photographed image for the blots can be obtained, if the photographed image for the texture has been obtained in step SS41. In contrast, the photographed image for the texture can be obtained, if the photographed image for the blots has been obtained in step SS41.

Next, the display control means 3*c* compares the wavelength components of the photographed images obtained in step SS41 and step SS44, and stores images having relatively more red components in a flash memory 4 as the image for the texture (step SS45), and images having relatively more blue components are stored in the flash memory (4) (step SS46). The order of executing step SS45 and step SS46 may be reversed.

Next, the display control means 3*c* associates the two types of photographed images for the texture and the blots, which have been photographed by the camera 2, with the LEDs 13, 12 and displays the images on the screen of the smartphone 1 (step SS47). Specifically, the images are displayed by determining whether the photographed image is the image for the texture taken using the LED 13 as the light source, or the image for the blots taken using the LED 12 as the light source.

Figure 11:
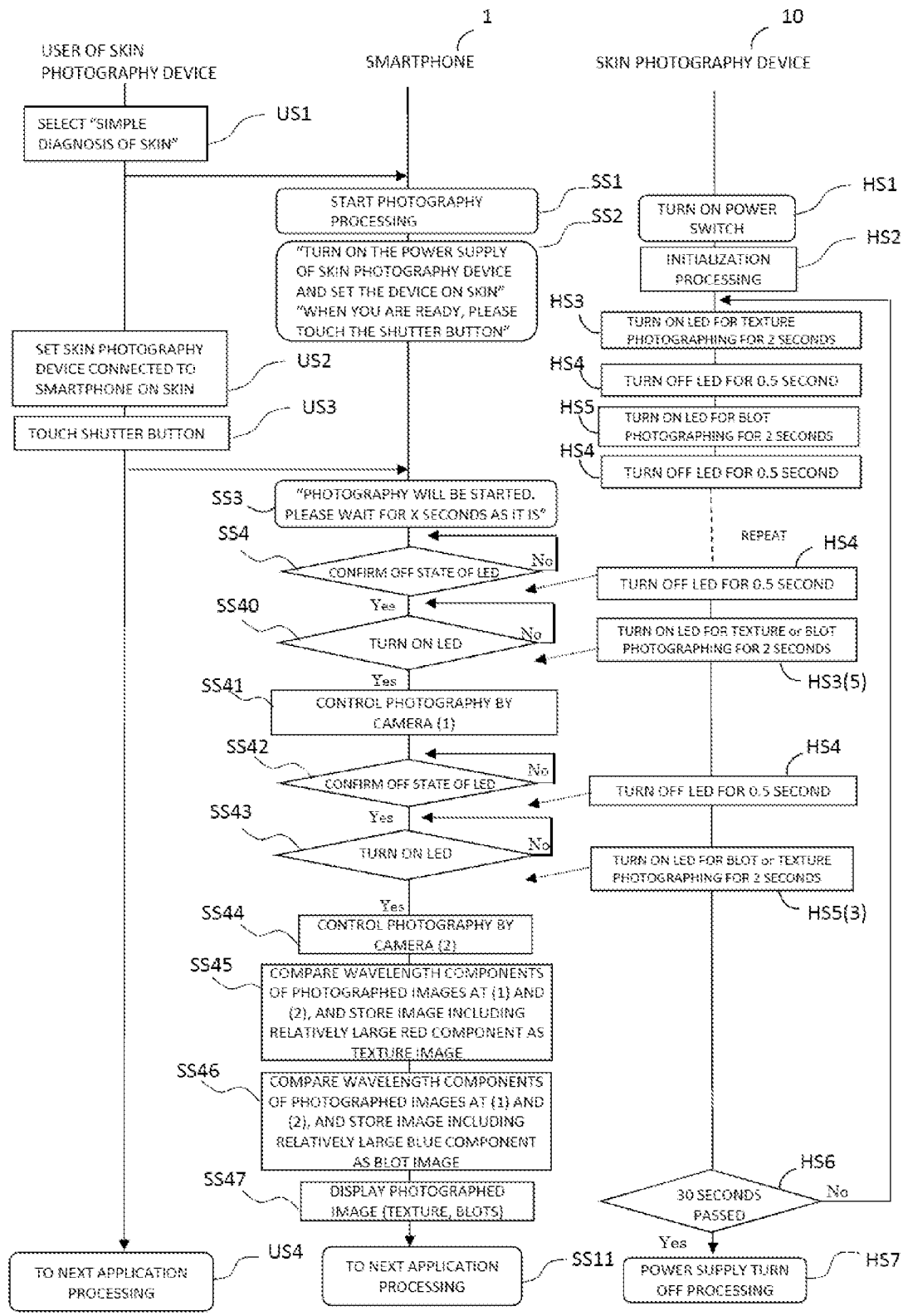
FIG. 11 is a flowchart of Example 4 for explaining an example of the above.

When the display is ended, the user selects ending the photography processing of the smartphone 1, restarting the photography, or selecting the next application processing by the user of skin photography device. The flowchart of FIG. 11 illustrates the case where the user of skin photography device selects the next application processing (US4) and the process proceeds to the next application processing (step SS11).

According to this example, a similar effect as in Example 4 can be obtained. In addition, it is not necessary to associate the photographed images with the LEDs 12, 13 during photography by the camera, because the obtained photographed images are associated with the LEDs 12, 13 according to the wavelength components and displayed on the screen. Thus, there is an advantage that an allowed deviation from a prescribed value of the LED can be increased to suppress the cost of the LED.

Example 5

In the above example, the off state of the LED 13 for texture photographing and the LED 12 for blot photographing is confirmed, followed by the detection of the wavelength of the LEDs and the confirmation of the lighting of the LED 13 for texture photographing, in order to control the photography by the camera 2. After that, the off state of the LED 13 for texture photographing and the LED 12 for blot photographing is confirmed, followed by the confirmation of the lighting of the LED 12 for blot photographing, in order to control the photography by the camera 2. In Example 5, however, only the first confirmation of the off state of the LEDs 12, 13 is carried out to increase the processing speed. The control sequence of this case will be described by referring to FIG. 12.

In this example, steps US1 to US4, steps SS1 to SS3, and steps HS1 to HS7 are similar to those in Example 1 and the description thereof will not be repeated.

In the smartphone 1, a standby state is entered, following step SS3, until the light on/off detection means 3a confirms the off state of the LEDs 12, 13 (step SS4). After the off state of the LEDs 12, 13 is confirmed in step SS4, the timer is started (timer is set to T=0) (step SS50). The timer is installed in the smartphone 1 as a clock function to allow the control means 3 to carry out ON/OFF control of the timer and detect elapsed time in the timer.

Next, the elapse of 1 second is waited after the timer is started (step SS50a), and when 1 second has passed, the light-off detection means 3a detects the on state of the LEDs 12, 13 and identifies the wavelengths of the LEDs 12, 13 (step SS51).

When the LED being turned on is the LED 12 for blot photographing, the photography control means 3b controls the photography by the camera 2 when 3.5 seconds has passed (T=3.5 (seconds)) after the start of the timer (step SS52). That is, the shutter of the camera 2 is released. By doing this, the photographed image for the blots can be obtained. Since the LED 12 is turned on for 2 seconds after the LEDs 12, 13 are turned off, the shutter of the camera 2 is released 0.5 to 1.0 second after the start of lighting of the LED 12, that is, almost in the middle (center point of time) of the time interval while the LED 12 is in the on state.

After 6.0 seconds (T=3.5+2.0+0.5) after the timer is started, the photography control means 3b controls the photography by the camera 2 (step SS53). That is, the shutter of the camera 2 is released. By doing this, the photographed image for the texture can be obtained. The LED 13 is turned on for 2 seconds after the LEDs 12, 13 are turned off, the LED 12 is turned on for 2 seconds, and the LEDs 12, 13 are turned off for 0.5 second. Thus, the shutter of the camera 2 is released 0.5 to 1.0 second after the start of lighting of the LED 13, that is, almost in the middle (center point of time) of the time interval while the LED 13 is in the on state.

In step SS51, if the LED being turned on is the LED 13 for texture photographing, the photography control means 3b controls the photography by the camera 2 at 3.5 seconds (T=3.5 (seconds)) after the start of the timer (step SS54). That is, the shutter of the camera 2 is released. By doing this, the photographed image for the texture can be obtained. Since the LED 13 is turned on for 2 seconds after the LEDs 12, 13 are turned off, the shutter of the camera 2 is released almost in the middle (center point of time) of the time interval while the LED 13 is in the on state.

After 6.0 seconds (T=3.5+2.0+0.5) after the timer is started, the photography control means 3b carries out the photography control of the camera 2 (step SS55). That is, the shutter of the camera 2 is released. By doing this, the photographed image for the blots can be obtained. Since the LED 12 is turned on for 2 seconds after the LEDs 12, 13 are turned off, the LED 13 is turned on for 2 seconds, and the LEDs 12, 13 and turned off for 0.5 second. Thus, the shutter of the camera 2 is going to be released almost in the middle (center point of time) of the time interval while the LED 12 is in the on state.

Next, the display control means 3c associates the two types of photographed images taken by the camera 2 for the texture and the blots, respectively, with the LEDs 13, 12 and displays the images on the screen of the smartphone 1 (step SS10). Specifically, the images are displayed by determining whether the photographed image is the image for the texture taken using the LED 13 as the light source, or the image for the blots taken using the LED 12 as the light source.

Figure 12:
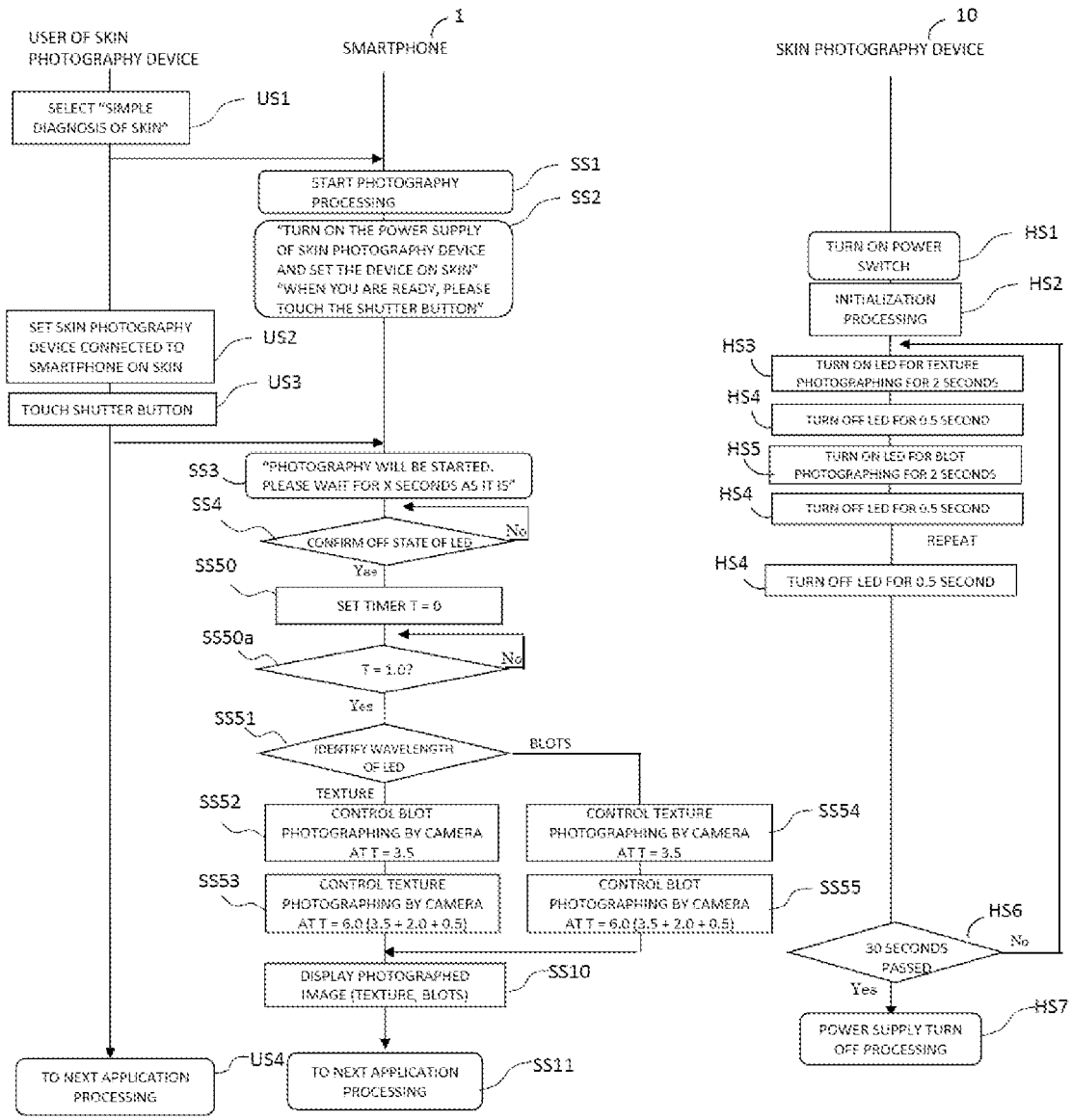
FIG. 12 is a flowchart of Example 5 for explaining an example of the above.

When the display is ended, the user selects ending the photography processing of the smartphone 1, restarting the photography, or selecting the next application processing by the user of skin photography device. The flowchart of FIG. 12 illustrates the case where the user of skin photography device selects the next application processing (US4) and the process proceeds to the next application processing (step SS11).

According to this example, a similar effect as in Example 1 can be obtained. In addition, the first confirmation of the off state of the LEDs 12, 13 is carried out to increase processing speed. Further, since the photographing by the camera 2 is carried out almost in the middle (center point of time) of the time interval while the LEDs 12, 13 are in the on state, it is possible to reliably carry out photography.

Example 6

In Example 2, turning off the LEDs 12, 13 for 0.5 second has been omitted. In Example 6, the identification of the wavelengths of the LEDs is also omitted. The control sequence of this case will be described by referring to FIG. 13.

In this example, steps US1 to US4, steps SS1 to SS3, and steps HS1 to HS7 are similar to those in Example 2 and the description thereof will not be repeated. However, the control on the side of the lens 10 for the skin is different from that of Example 2 in that, subsequent to the initialization processing, the CPU (light source control means) 16 repeatedly controls the LEDs 13, 12 to turn off first for a predetermined time period (0.5 second) (step SS15), followed by turning on of the two types of LEDs 13, 12 successively for a predetermined time period (2 seconds). After the turning on of the LEDs 13, 12, the LEDs 12, 13 are turned off for the predetermined time period (0.5 second).

In the smartphone 1, after the light on/off detection means 3a has confirmed the off state of the LEDs 12, 13 (step SS61) subsequent to steps SS1 to SS3, the timer is started (timer is set to T=0) (step SS62).

At 1 second after the start of the timer (T=1.0 (second)), the photography control means 3b controls the photography by the camera 2 (step SS63). That is, the shutter of the camera 2 is released. By doing this, the photographed image for the texture can be obtained. Specifically, the photographed image for the texture can be obtained by releasing the shutter of the camera 2, as the LED 13 for texture photographing is first turned on after the LEDs 12, 13 are turned off. Since the LED 13 is turned on for 2 seconds after the LEDs 12, 13 are turned off, the shutter of the camera 2 is released almost in the middle (center point of time) (0.5 to 1.0 second after the start of lighting) of the 2 seconds while the LED 13 is in the on state.

Next, at 3.0 seconds (T=1.0+2.0) after the start of the timer, the photography control means 3b controls the photography by the camera 2 (step SS64). That is, the shutter of the camera 2 is released. By doing this, the photographed image for the blots can be obtained. Since the LED 12 is turned on for 2 seconds after the LEDs 12, 13 are turned off and the LED 13 is turned on for 2 seconds, the shutter of the camera 2 is released almost in the middle (center point of time) (0.5 to 1.0 second after the start of lighting) of the time interval while the LED 12 is in the on state.

Next, the display control means 3c associates the two types of photographed images taken by the camera 2 for the texture and the blots, respectively, with the LEDs 13, 12 and displays the images on the screen of the smartphone 1 (step SS10). Specifically, the images are displayed by determining whether the photographed image is the image for the texture taken using the LED 13 as the light source, or the image for the blots taken using the LED 12 as the light source.

Figure 13:
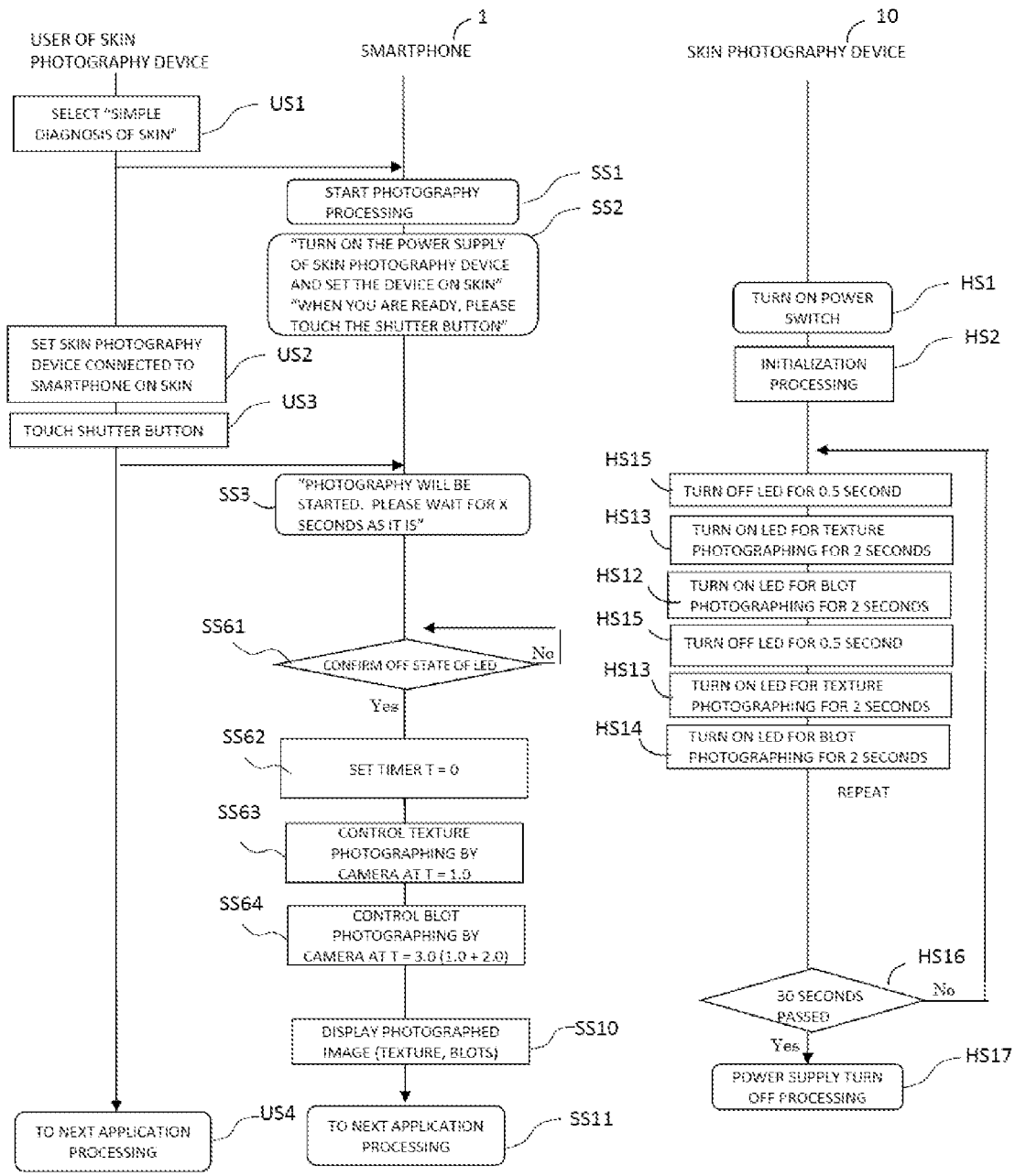
FIG. 13 is a flowchart of Example 6 for explaining an example of the above.

When the display is ended, the user selects ending the photography processing of the smartphone 1, restarting the photography, or selecting the next application processing by the user of skin photography device. The flowchart of FIG. 13 illustrates the case where the user of skin photography device selects the next application processing (US4) and the process proceeds to the next application processing (step SS11).

According to this example, a similar effect as in Example 2 can be obtained, and an advantage of reliably carrying out photography, because the photography by the camera 2 is carried out in the middle (center point of time) of the time interval while the LEDs 12, 13 are in the on state, can also be obtained.

In Examples 5 and 6, the photography by the camera is controlled 0.5 second after the start of lighting of the LED at the earliest. However, the photography by the camera may be started when the lighting of the LED is started, because the photography cannot be started 0.0 second after the start of controlling the photography by the camera.

Further, in Examples 1 to 6 of the first embodiment, upon turning on of the power supply of the lens 10 for the skin, the LEDs 12, 13 are configured to be turned on alternately and then turned off after the predetermined time period has passed. It is possible to prevent consumption of the battery by the following procedures.

Specifically, the lens 10 for the skin may be provided with an illumination detection apparatus or a dual-tone multi-frequency (DTMF) detection apparatus to recognize touching of the shutter button, and the flash light may be emitted or the sound of a predetermined musical scale (a musical scale that is hardly confused with environmental noise and easily detected by the detection apparatus) may be generated. The LED 13 for texture photographing is then turned on for 2 seconds and the LED 13 for blot photographing is turned on for 2 seconds. The shutter is released at the center point of time of the 2 seconds for each LED to prevent consumption of the battery.

In this example, the LED of the lens for the skin is automatically turned off 30 seconds after turning on of the power switch to suppress the power consumption caused by forgetting turning off of the light. Alternatively, it may be possible to automatically turn off the light in 15 seconds if the user has been accustomed to the photography. The time may be freely set by operating the application by the user.

In Examples 1 to 6, the lens 10 for the skin is provided with the switching means that is manually turned on/off, such that the user may turn on the switch by hand before photography to start the light on/off control of the LEDs 12, 13. Further, it may also possible to turn on a second switch automatically (without intentionally operating the switch to turn on by the user) to start the light on/off control of the LEDs 12, 13 by bringing the camera for the skin to the skin by the user. As a result, the power consumption is suppressed and the operability by the user is improved, such that the influence of the natural light can be reduced as follows. The main switch may be eliminated and replaced by the second switch means.

The second automatic switch means may include the following:

(1) One or more push switches that elastically project by about 1.0 mm may be provided at equal intervals at a portion where the lens for the skin comes in contact with the skin (on the surface of the abutting portion 20b of FIG. 2).

In this case, it may be configured that the CPU 16 detects the pressing of the push switch when the abutting portion 20b comes to abut against the skin, and the CPU 16 turns on the switch (power switch 19). When the CPU 16 detects that the abutting portion 20b is detached from the skin and the push switch is reset by elastic return force, the CPU 16 turns off the switch (power supply switch 19).

(2) A photo sensor is provided inside a lens barrel where the light is shielded. When a bright state is switched to a dark state, that is, the abutting portion 20b abuts against (seals) the skin to switch the inside state of the lens barrel from the bright state to the dark state, this is recognized as turning on of the switch and the control is carried out. In the opposite case, when the abutting portion 20b is detached from the abutting portion 20b and the inside state of the lens barrel is switched from the bright state from the dark state, this is recognized as turning off of the switch and the control is carried out.

In this case, it may be configured that the CPU 16 detects switching of the inside state of the lens barrel from the bright state to the dark state according to a signal from the photo sensor, and the CPU 16 turns on the switch (power switch 19). In contrast, when the CPU 16 detects the switching of the inside state of the lens barrel from the dark state to the bright state, the CPU 16 turns off the switch (power switch 19).

The on/off state of the LEDs 12, 13 is identified depending on whether an image received by the camera is bright or dark. However, it is necessary to be careful for the case where the bright state is caused by the entering of the natural light other than the lighting of the LEDs 12, 13. Bright case modes and dark case modes are listed in Table 1 below.

TABLE 1

| | State matrix | | | |
| --- | --- | --- | --- | --- |
| State No. | Closeness of lens to skin | On/off state of LED | Natural light incident on lens | Image received by camera |
| 1 | Yes | On | No | Bright |
| 2 | Yes | Off | No | Dark |
| 3 | No | On | Yes | Bright |
| 4 | No | On | No | Dark |
| 5 | No | Off | Yes | Bright |
| 6 | No | Off | No | Dark |

State Nos. 1 and 2 are normal photography states, but when the lens is not in close contact with the skin as in state Nos. 3 to 6, the brightness of the image received by the camera depends on the presence or absence of the natural light incident on the lens.

To reduce erroneous identification in the state Nos. 3 to 6, a switch may be provided at a portion of the lens which is in close contact with the skin to turn on the power switch of the skin photographing apparatus and start blinking processing of the LED by bringing the lens to be in close contact with the skin. A photographing processing of this case proceeds as illustrated in Table 2.

TABLE 2

| No. | Operation by user | Processing in smartphone |
|---|---|---|
| 1 | Start application | Display photographing instruction: "example: put the lens on photographing spot of the face and touch (anywhere of) the screen" |
| 2 | | |
| 3 | Set lens for skin on skin (switch of lens for skin is turned on and LEDs start lighting alternately) | |
| 4 | Touch screen | |
| 5 | | Photographing processing (sound or voice guidance of end of processing) |
| 6 | Detach lens for skin from skin (switch of lens for skin is turned off) | |
| 7 | Confirm photographed image on screen | |

When the photographing processing is carried out at No. 5 of Table 2, the processing can be carried out by assuming that the lens is in close contact with the skin and no incident natural light is present. If a system in which the power switch of the lens 10 for the skin is turned on while the lens 10 for the skin is in close contact with the skin is not adopted, it may happen that 30 seconds have already passed and the LED is no longer lighted when the lens for the skin is abutted against the skin after turning on of the power switch. Such a problem does not occur when this system is adopted.

Example 7

In Examples 1 to 4, the identification of the LED 13 for the texture and the LED 12 for the blots is carried out according to the wavelengths of the LEDs 12, 13. Alternatively, the identification of the LED may be carried out according to the timing of turning on/off the LEDs 12, 13.

Figure 14:
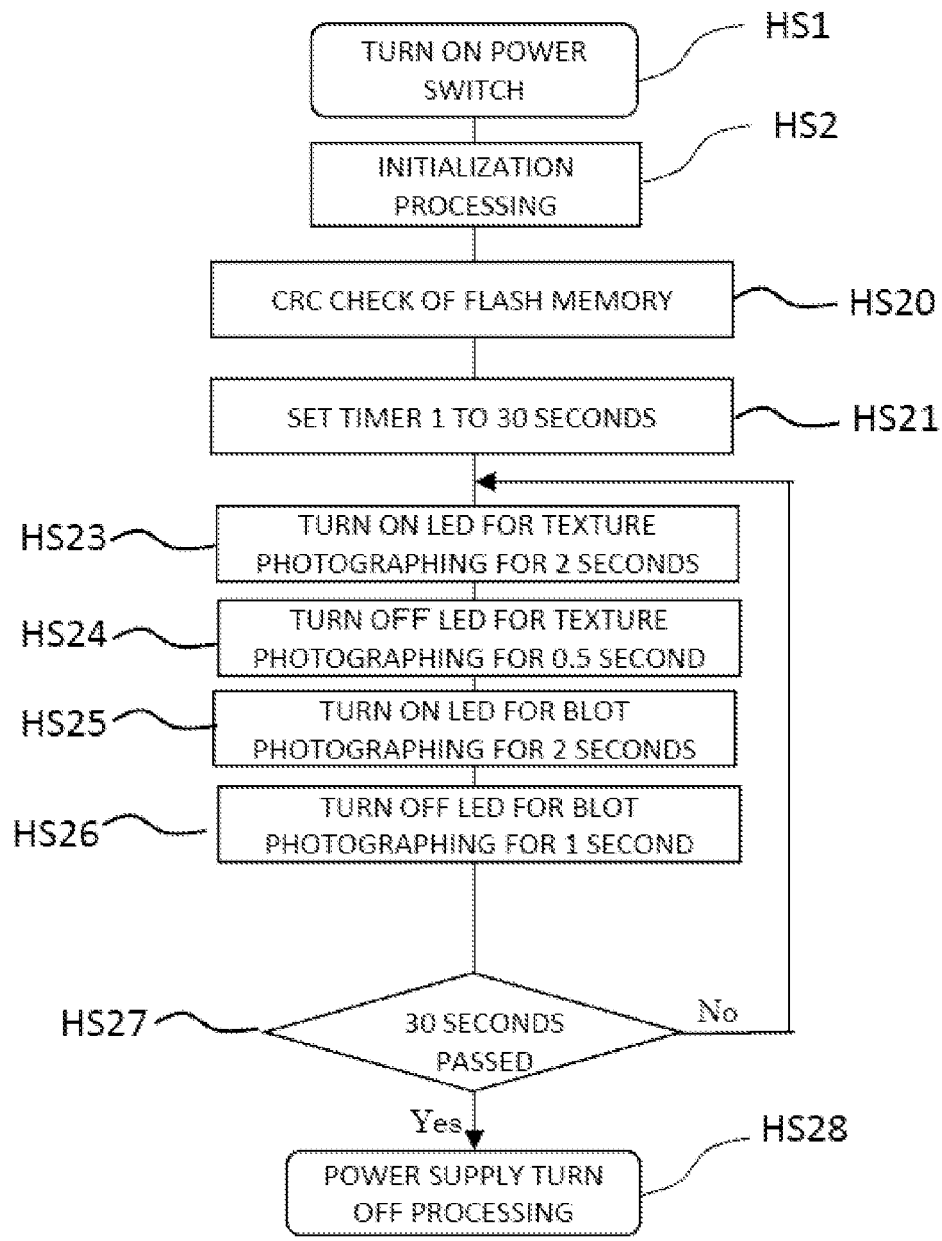
FIG. 14 is a flowchart of Example 7 of the above illustrating the processing on the side of a lens for skin.
Figure 15:
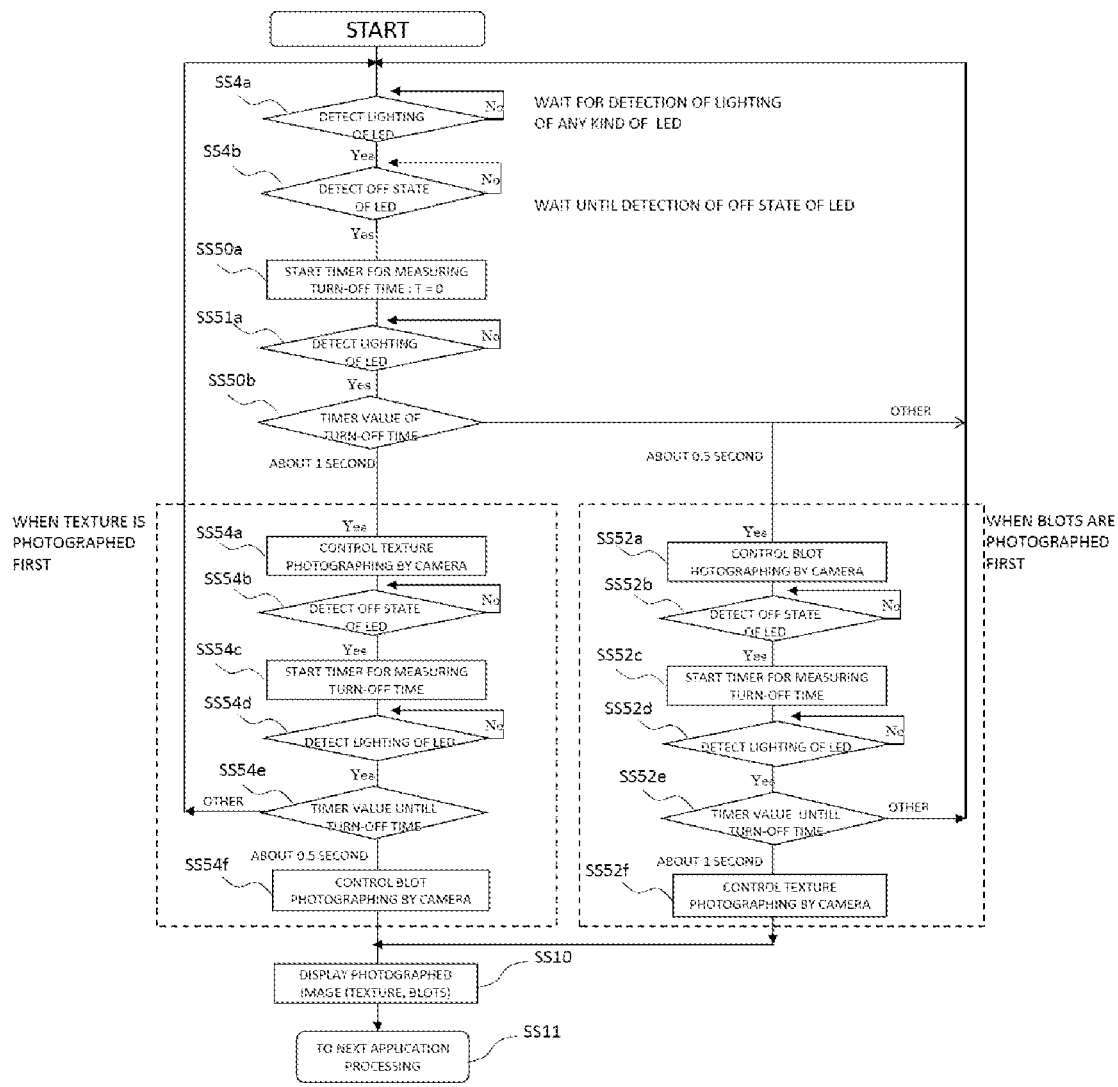
FIG. 15 is a flowchart of Example 7 of the above illustrating the processing on the side of a smartphone.

FIGS. 14 and 15 illustrate the processing sequence of Example 7. In Example 7, the LEDs 12, 13 are identified by the length of the off state time. FIG. 14 illustrates the processing sequence on the side of the skin measuring apparatus (the lens 10 for the skin). FIG. 15 illustrates the processing sequence on the side of the smartphone 1. Although it is assumed that, when abutted against the skin, the skin measuring apparatus 10 automatically turns on the power switch 19 as described above, but may also turn on the power switch by hand as descried above.

In this example, steps US1 to US4 and steps SS1 to SS3 are similar to those in Example 5 and the description thereof will not be repeated.

As illustrated in FIG. 14, on the side of the lens 10 for the skin (skin measuring apparatus), when the user brings the camera for the skin to be in contact with the skin, the power switch is automatically turned on (without intentionally operated to turn on the switch by the user) (HS1), and the initialization processing is carried out (HS2). After a CRC check of the flash memory 4 is carried out (step HS20), the timer is set to 30 seconds (step HS21).

After the LED 13 for texture photographing is turned on for 2 seconds (step HS23), the LED 13 is turned off for 0.5 second (step HS24). After the LED 12 for blot photographing is turned on for 2 seconds (step HS25), the LED 12 is turned off for 1 second (step HS26).

Subsequently, steps HS23 to HS26 are carried out successively and repeatedly and, when 30 seconds has passed (step HS27) after the timer is set (step HS21), the CPU 16 turns off the power supply (step HS28). If 30 seconds has not been passed in step HS27, steps HS23 to HS26 are carried out successively and repeatedly and, when 30 seconds has passed (step HS27), the CPU 16 turns off the power supply (HS28).

Thus, the LED 13 for the texture is turned on for 2 seconds and then turned off for 0.5 second, and the LED 12 for the blots is turned on for 2 seconds and then turned off for 1 second. It is possible, therefore, to identify which LED is in the on state according to the length of the off state time.

As illustrated in FIG. 15, the smartphone 1 enters the standby state, after step SS3, until the light on/off detection means 3a detects the on state of either the LED 12 or 13 (step SS4a). After the on state of the LED is detected, the standby state is entered until the off state of the LED having been turned on is detected (step SS4b).

After the off state of the LEDs is confirmed in step SS4b, the timer is started (timer is set to T=0) (step SS50a). The timer measures the off time of the LEDs.

The timer is installed in the smartphone 1 as a clock function to allow the control means 3 to carry out on/off control of the timer and detect the elapsed time in the timer.

When the on state of the LED is detected (step SS51a), the timer measures time between the turning off of the LED in step SS4b and the turning on of the LED in step SS51a to obtain a timer value (off state time) (step SS50b).

If the timer value obtained in step SS50b is about 0.5 second, this indicates that the LED 13 for the texture is in the off state. Subsequently, the LED 12 for the blots is going to be turned on. Thus, the photography control means 3b controls the photography by the camera 2 at appropriate time during the on state by considering the lighting time (2 seconds) of the LED 12 (step SS52a). That is, the shutter of the camera 2 is released. By doing this, the photographed image for the blots can be obtained.

If the timer value obtained in step SS50b is about 1.0 second, the process proceeds to processing described later (step SS54a). If the timer value is other than about 0.5 second or about 1.0 second, the process returns to step SS4a.

Then, after the off state of the LED 12 is confirmed (step SS52b), the timer is started (timer is set to T=0) (step SS52c). The timer measures the off state time of the LED 12.

When the on state of the LED 12 is detected (step SS52d), the timer measures time between the turning off of the LED 12 in step SS52b and the turning on of the LED 13 to obtain a timer value (off state time) (step SS52e).

If the timer value obtained in step SS52e is about 1.0 second, this indicates that the LED 12 for the blots is in the off state. Subsequently, the LED 13 for the texture is going to be turned on. Thus, the photography control means 3b controls the photography by the camera 2 at appropriate time during the on state by considering the lighting time (2 seconds) of the LED 13 (step SS52*f*). That is, the shutter of the camera 2 is released. By doing this, the photographed image for the texture can be obtained.

If the timer value obtained in step SS52*e* is other than about 1.0 second, the process returns to step SS4*a*.

If the timer value obtained in step SS50*b* is about 1.0 second, this indicates that the LED 12 for the blots is in the off state. Subsequently, the LED 13 for the texture is going to be turned on. Thus, the photography control means 3*b* controls the photography by the camera 2 at appropriate time during the on state by considering the lighting time (2 seconds) of the LED 13 (step SS54*a*). That is, the shutter of the camera 2 is released. By doing this, the photographed image for the texture can be obtained.

Then, after the off state of the LED 13 is confirmed (step SS54*b*), the timer is started (timer is set to T=0) (step SS54*c*). The timer measures the off state time of the LED 13.

When the on state of the LED 13 is detected (step SS54*d*), the timer measures time between the turning off of the LED 13 in step SS54*b* and the turning on of the LED 12 to obtain a timer value (off state time) (step SS54*e*).

If the timer value obtained in step SS54*e* is about 0.5 second, this indicates that the LED 13 for the texture is in the off state. Subsequently, the LED 12 for the blots is going to be turned on. Thus, the photography control means 3*b* controls the photography by the camera 2 at appropriate time during the on state by considering the lighting time (2 seconds) of the LED 12 (step SS54*f*). That is, the shutter of the camera 2 is released. By doing this, the photographed image for the blots can be obtained.

If the timer value obtained in step SS54*e* is other than about 0.5 second, the process returns to step SS4*a*.

Next, the display control means 3*c* associates the two types of photographed images taken by the camera 2 for the texture and the blots, respectively, with the LEDs 13, 12 and displays the images on the screen of the smartphone 1 (step SS10). Specifically, the images are displayed by determining whether the photographed image is the image for the texture taken using the LED 13 as the light source, or the image for the blots taken using the LED 12 as the light source.

When the display is ended, the user selects ending the photography processing of the smartphone 1, restarting the photography, or selecting the next application processing by the user of skin photography device. The flowchart of FIG. 15 illustrates the case where the user of skin photography device selects the next application processing (US4) and the process proceeds to the next application processing (step SS11).

According to this example, the identification of the LED is carried out according to the timing of turning on/off the LEDs 12, 13 to increase the processing speed.

Although the off state time is different for the LEDs 12, 13, it may also be possible to provide an identical off state time for the LEDs 12, 13, while providing different lighting time for the LED 13 for the texture and the LED 12 for the blots of, e.g., 1.5 seconds and 2.0 seconds, respectively. By measuring the lighting time of the LED that is turned on after the first off state, it is determined which of the LED 13 for the texture and the LED 12 for the blots has been turned on to start photography next time the LED is turned on.

Example 8

This example is made from Example 7 combined with identification according to the wavelengths of the LEDs. It is possible to eliminate erroneous photography when the wavelength of the natural light is incidentally identical to the wavelengths of the LED for the texture and the LED for the blots, or when the brightening/darkening timing of the natural light is incidentally identical to the turning on/off timing of the LEDs.

The processing sequence on the side of the lens 10 for the skin (skin measuring apparatus) is the same as that of Example 7 illustrated in FIG. 14, and the description thereof will not be repeated.

The processing sequence on the side of the smartphone 1 will be described below.

Figure 16:
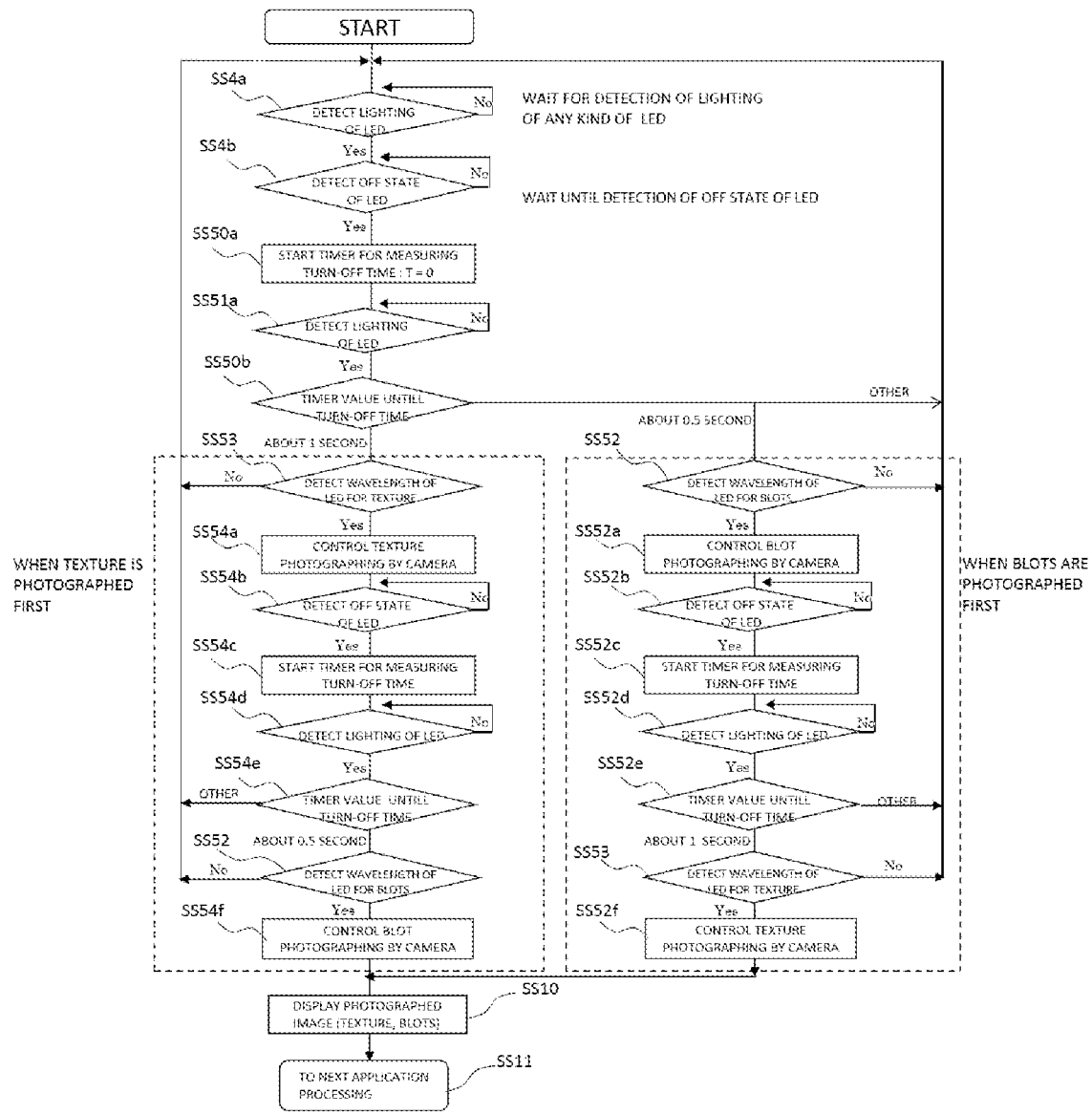
FIG. 16 is a flowchart of Example 8 of the above illustrating the processing on the side of the smartphone.

As illustrated in FIG. 16, the process proceeds from step SS4*a* to steps SS4*b*, SS50*a*, SS51*a*, and SS50*b*, in the smartphone 1, as in Example 7 illustrated in FIG. 15.

If the timer value obtained in step SS50*b* is about 0.5 second, the light on/off detection means 3*a* detects the on state of the LED 12 by detecting the wavelength of light of the LED 12 for blot photographing (step SS52). When the on state of the LED 12 is detected, the photography control means 3*b* controls the photography by the camera 2 at appropriate time while the LED 12 is in the on state (step SS52*a*). That is, the shutter sound of the camera 2 is generated to capture a still image. By doing this, the photographed image for the blots can be obtained.

Then, after the off state of the LED 12 is confirmed (step SS52*b*), the timer is started (timer is set to T=0) (step SS52*c*). The timer measures the off state time of the LED 12.

When the on state of the LED 12 is detected (step SS52*d*), the timer measures time between the turning off of the LED 12 in step SS52*b* and the turning on of the LED 13 to obtain a timer value (off state time) (step SS52*e*).

If the timer value obtained in step SS52*e* is about 1.0 second, this indicates that the LED 12 for the blots is in the off state. Subsequently, the LED 13 for the texture is going to be turned on.

The light on/off detection means 3*a* detects the on state of the LED 13 by detecting the wavelength of light of the LED 13 for texture photographing (step SS53). When the on state of the LED 13 is detected, the photography control means 3*b* controls the photography by the camera 2 at appropriate time while the LED 13 is in the on state (step SS52*f*). That is, the shutter sound of the camera 2 is generated to capture a still image. By doing this, the photographed image for the texture can be obtained.

If the timer value obtained in step SS50*b* is about 1.0 second, the light on/off detection means 3*a* detects the on state of the LED 13 for texture photographing by detecting the wavelength of light of the LED 13 (step SS53). When the on state of the LED 13 is detected, the photography control means 3*b* controls the photography by the camera 2 at appropriate time while the LED 13 is in the on state (step SS54*a*). That is, the shutter sound of the camera 2 is generated to capture a still image. By doing this, the photographed image for the texture can be obtained.

After the off state of the LED 13 is detected (step SS54*b*), the timer is started (timer is set to T=0) (step SS54*c*). The timer measures the off state time of the LED 13.

When the on state of the LED 13 is detected (step SS54*d*), the timer measures time between the turning off of the LED 13 in step SS54*b* and the turning on of the LED 12 to obtain a timer value (off state time) (step SS54*e*).

If the timer value obtained in step SS54*e* is about 0.5 second, this indicates that the LED 13 for the texture is in the off state. Subsequently, the LED 12 for the blots is going to be turned on.

The light on/off detection means 3*a* detects the on state of the LED 12 for blot photographing by detecting the wavelength of light of the LED 12 (step SS52). When the on state of the LED 12 is detected, the photography control means 3b controls the photography by the camera 2 at appropriate time while the LED 12 is in the on state (step SS54f). That is, the shutter sound of the camera 2 is generated to capture a still image. By doing this, the photographed image for the blots can be obtained.

Next, the display control means 3c associates the two types of photographed images taken by the camera 2 for the texture and the blots, respectively, with the LEDs 13, 12 and displays the images on the screen of the smartphone 1 (step SS10). Specifically, the images are displayed by determining whether the photographed image is the image for the texture taken using the LED 13 as the light source, or the image for the blots taken using the LED 12 as the light source.

When the display is ended, the user selects ending the photography processing of the smartphone 1, restarting the photography, or selecting the next application processing by the user of skin photography device. The flowchart of FIG. 16 illustrates the case where the user of skin photography device selects the next application processing (US4) and the process proceeds to the next application processing (step SS11).

According to this example, the on state of the LEDs 12, 13 is detected by detecting the wavelengths of light of the LEDs 12, 13 by the light on/off detection means 3a. There is an advantage, therefore, that the erroneous photography can be eliminated when the wavelength of the natural light is incidentally identical to the wavelengths of the LED 13 for the texture and the LED 12 for the blots, or when the brightening/darkening timing of the natural light is incidentally identical to the turning on/off timing of the LEDs 12, 13.

In Examples 7 and 8, although the LEDs are identified by the length of the off state time, the types of the LEDs may be identified by measuring the lighting time of the LED.

In the description of Example 8 or the like, such phrases as detection of the wavelengths, detection of the LED for the blots, etc. have been used, but it would be preferable in the actual processing to use colors that change according to the wavelength, instead of measuring the wavelengths themselves.

Second Embodiment

Figure 17:
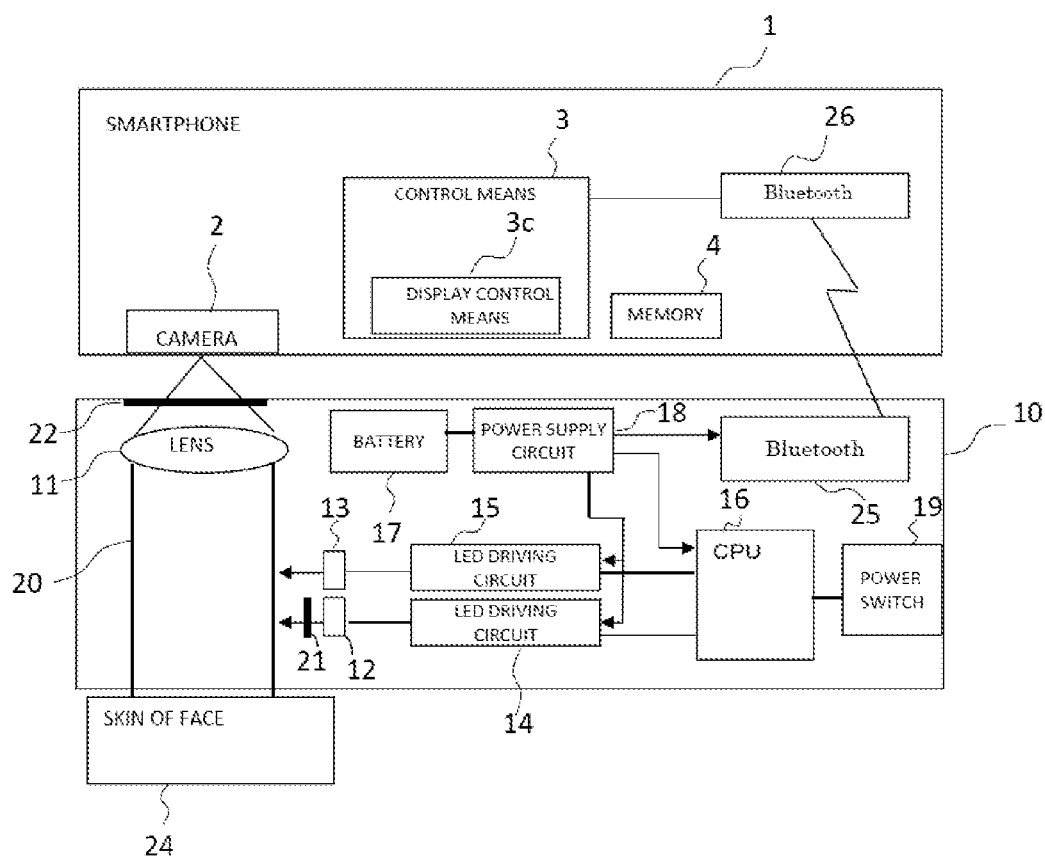
FIG. 17 is a block diagram illustrating a portable photography device according to a second embodiment of the present invention.

FIG. 17 is a block diagram illustrating a portable photography device according to a second embodiment of the present invention. The portable photography device according to the present embodiment differs from the portable photography device according to the first embodiment in that transmission/reception means is provided in the smartphone 1 and the lens 10 for the skin (lens module) to allow transmission/reception of data and signals to and from these constituent components. This point, therefore, will be described in detail below. The same reference signs are given to the constituent components similar to those in the first embodiment and the description thereof will not be repeated or otherwise provided in a simplified manner.

The lens 10 for the skin (lens module) includes transmission/reception means 25 that receives a light-source turn-on instruction signal and a light-source turn-off instruction signal from the smartphone 1, while transmitting a light-source turn-on reporting signal and a light-source turn-off reporting signal to the smartphone 1. The transmission/reception means 25 is formed, for example, by a Bluetooth module 25 which is controlled by the CPU 16.

The light-source turn-on instruction signal is a signal to turn on the LEDs 12, 13, while the light-source turn-off instruction signal is a signal to turn off the LEDs 12, 13. The light-source turn-on reporting signal is a signal to report that the LEDs 12, 13 have been turned on, while the light-source turn-off reporting signal is a signal to report that the LEDs 12, 13 have been turned off.

The CPU (light source control means) 16 is configured to turn on the LEDs 12, 13 and cause the transmission/reception means 25 to transmit the light-source turn-on reporting signal to the smartphone 1 when the light-source turn-on instruction signal is received from the smartphone 1 via the transmission/reception means 25. When the light-source turn-off instruction signal is received from the smartphone 1 via the transmission/reception means 25, the CPU 16 turns off the LEDs 12, 13 and cause the transmission/reception means to transmit the light-source turn-off reporting signal to the smartphone 1.

The smartphone 1 includes transmission/reception means 26 of the smartphone (transmission/reception means on the terminal side) that receives the light-source turn-on reporting signal and the light-source turn-off reporting signal from the transmission/reception means 25 of the lens (lens module) 10 for the skin, and transmits the light-source turn-on instruction signal and the light-source turn-off instruction signal to the lens (lens module) 10 for the skin (hereinafter the transmission/reception means 26 of the smartphone will be referred to as the transmission/reception means 26). The transmission/reception means 26 includes, for example, a Bluetooth module 26 which is controlled by the control means 3.

The control means 3 is configured to cause the camera 2 to carry out photography when the light-source turn-on reporting signal is received from the lens (lens module) 10 for the skin via the transmission/reception means 25, 26. When the photography by the camera 2 is ended, the light-source turn-off instruction signal is transmitted to the lens (lens module) 10 for the skin via the transmission/reception means 25, 26. When the light-source turn-off reporting signal is received from the lens (lens module) 10 for the skin via the transmission/reception means 26, 25, the light-source turn-on instruction signal is transmitted to the lens (lens module) 10 for the skin via the transmission/reception means 25, 26.

The display control means 3c is also configured to associate the photographed image taken by the photography control means 3b with the LEDs 12, 13 and displays the image on the screen of the smartphone 1.

Figure 18:
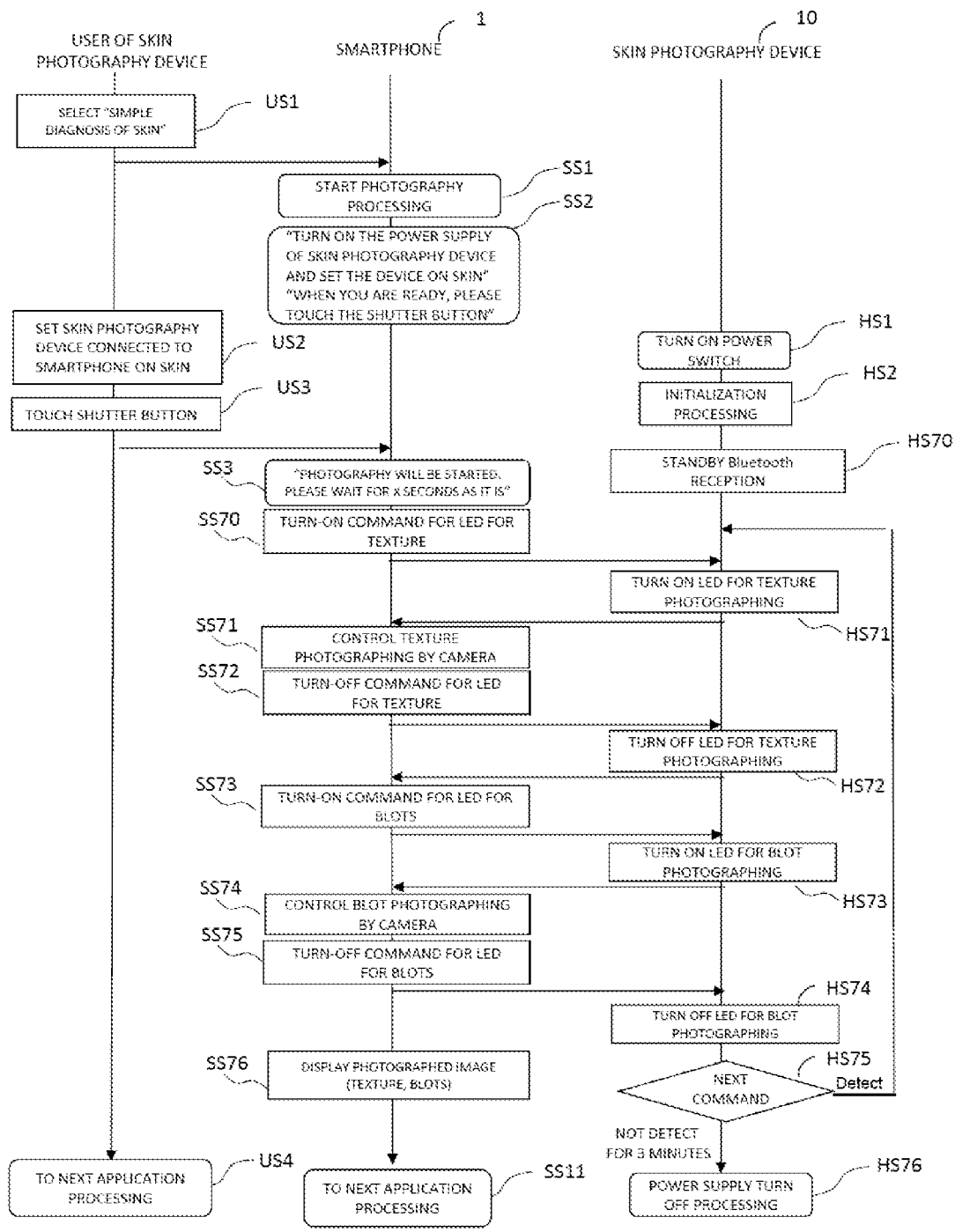
FIG. 18 is a flowchart illustrating an example of photographing skin of a face of a person with the portable photography device according to the second embodiment of the present invention.

Next, an example of a control sequence of a method of photographing skin of a face of a person by the portable photography device of the second embodiment will be described by referring to FIG. 18.

First, a user of skin photography device (user) turns on the power supply of the smartphone 1 and selects a "simple diagnosis of skin" application on the screen (step US1).

Accordingly, photographing processing of the smartphone 1 is started (step SS1). On the screen of the smartphone 1, a message saying "Turn on the power supply of the skin photography device and set the device on the skin. Touch the shutter button when you are ready" is displayed (step SS2).

A user of skin photography device then sets the skin photography device connected to the smartphone on the skin (step US2) and touches the shutter button displayed on the screen of the smartphone (step US3).

In the lens 10 for the skin, when the power switch is turned on (step HS1), the lens 10 for the skin is subjected to initialization processing (step HS2), and the transmission/reception means 25 formed by the Bluetooth module enters a reception standby state (step HS70).

During the initialization processing of the lens 10 for the skin, a message saying "Photography will be started. Do not move and wait for X seconds as it is." is displayed on the screen of the smartphone 1 (step SS3).

When the user of skin photography device (user) touches the shutter button on the screen of the smartphone 1, the control means 3 of the smartphone 1 generates a turn-on command (light-source turn-on instruction signal) to turn on the LED 13 for texture photographing (step SS70). The turn-on command is transmitted as a signal from the transmission/reception means 26, and this signal is received by the transmission/reception means 25 of the lens 10 for the skin. By receiving the turn-on command, the LED 13 for texture photographing is turned on (step HS71). When the LED 13 for texture photographing is turned on, an LED turn-on reporting signal (light-source turn-on reporting signal) is transmitted to the smartphone 1 from the transmission/reception means 25 of the lens 10 for the skin. When the smartphone 1 receives the LED turn-on reporting signal via the transmission/reception means 26, the control means 3 controls the photography by the camera 2 (step SS71). That is, the shutter of the camera 2 is released. By doing this, the photographed image for the texture can be obtained.

After the photographed image for the texture has been taken by the camera 2, the control means 3 of the smartphone 1 generates a turn-off command (light-source turn-off instruction signal) to turn off the LED 13 for texture photographing (step SS72). The turn-off command is transmitted as a signal from the transmission/reception means 26, and this signal is received by the transmission/reception means 25 of the lens 10 for the skin. By receiving the turn-off command, the LED 13 for texture photographing is turned off (step HS72).

When the LED 13 for texture photographing is turned off, an LED turn-off reporting signal (light-source turn-off reporting signal) is transmitted to the smartphone 1 from the transmission/reception means 25 of the lens 10 for the skin. By receiving the LED turn-off reporting signal, the control means 3 generates the turn-on command (light-source turn-on instruction signal) to turn on the LED 12 for blot photographing (step SS73). The turn-on command is transmitted as a signal from the transmission/reception means 26, and this signal is received by the transmission/reception means 25 of the lens 10 for the skin. By receiving the turn-on command, the LED 12 for blot photographing is turned on (step HS73).

When the LED 12 is turned on, the LED turn-on reporting signal (light-source turn-on reporting signal) is transmitted to the smartphone 1 from the transmission/reception means 25 of the lens 10 for the skin. When the smartphone 1 receives the LED turn-on reporting signal via the transmission/reception means 26, the control means 3 controls the photography by the camera 2 (step SS74). That is, the shutter of the camera 2 is released. By doing this, the photographed image for the blots can be obtained.

Next, the control means 3 generates the turn-off command (light-source turn-off instruction signal) to turn off the LED 12 for blot photographing (step SS75). The turn-off command is transmitted from the transmission/reception means 26 as a signal and received by the transmission/reception means 25 of the lens 10 for the skin. By receiving the turn-off command, the LED 12 for blot photographing is turned off (step HS74).

It is determined in the lens 10 for the skin whether the turn-on command of the LED 13 for the texture is transmitted from the smartphone 1 in step HS75. When the turn-on command is transmitted, the process returns to the step HS71 and carries out similar processing. If the turn-on command is not transmitted, the power supply is turned off (step HS76) and the process is ended (step HS76).

Meanwhile, in the smartphone 1, the display control means 3c associates the two types of photographed images for the texture and the skin taken by the camera 2 with the LEDs 13, 12 and displays the images on the screen of the smartphone 1 (step SS76). Specifically, the images are displayed by determining whether the photographed image is the image for the texture taken using the LED 13 as the light source, or the image for the blots taken using the LED 12 as the light source.

Since the image photographed by the camera 2 in step SS71 is for the texture and the image photographed by the camera 2 in step SS74 is for the blots, the individual images photographed by the camera 2 are separately stored in the memory 4 for the texture and the blots. By reading the individual image from the memory 4, it is therefore possible to display the photographed image for the texture and the photographed image for the blots on the screen of the smartphone 1.

When the display is ended, the photography processing is ended in the smartphone 1 or the user of skin photography device selects the next application processing (US4) to move the process to the next application processing (step SS11).

According to the present embodiment, the light source control means (CPU) 16 of the lens 10 for the skin turns on the LEDs 12, 13 when the light-source turn-on instruction signal is received from the smartphone 1 is the transmission/reception means 26, 25, while transmitting the light-source turn-on reporting signal to the smartphone 1 by the transmission/reception means 25. Thus, it is possible to turn on the LEDs 12, 13 at appropriate timing according the photography by the camera 2.

The light source control means 16 also turns off the LEDs 12, 13 upon receiving the light-source turn-off instruction signal via the transmission/reception means 26, 25, while transmitting the light-source turn-off reporting signal to the smartphone 1 by the transmission/reception means 25. Thus, it is possible to turn off the light sources at appropriate timing when the photography of the camera is ended.

Further, the photography control (photographing) of the camera 2 is carried out when the control means 3 of the smartphone 1 receives the LED turn-on reporting signal (light-source turn-on reporting signal) from the lens 10 for the skin via the transmission/reception means 25, 26. Thus, it is possible to reliably photographing the skin as the object by the camera 2.

After the photographing by the camera 2, the LED turn-off instruction signal to the lens 10 for the skin via the transmission/reception means 26, 25. Thus, it is possible to reliably turn off the LEDs 12, 13 to prevent consumption of the battery.

The photographed image taken by the camera 2 is associated with the LEDs 12, 13 and displayed on the screen of the smartphone 1 by the display control means 3c. Thus, it is possible for the user to easily confirm whether the photographed image displayed on the screen is the photographed image for the texture or the photographed image for the blots.

In the first and second embodiments described above, the smartphone 1 including a digital camera has been described as an example of the portable terminal, but the portable terminal with the camera is not limited to the smartphone 1. Alternatively, for example, an ordinary portable phone including a digital camera or a tablet including a digital camera may be used.

In the second embodiment, the Bluetooth modules 25, 26, which is one of wireless communication systems, has been adopted as the transmission/reception means capable of transmitting/receiving data or signals between the smartphone 1 and the lens (lens module) 10 for the skin. However, the transmission/reception means 25, 26 are not limited to those using wireless communications, and may be realized by a wired communication system, such as USB connection.

REFERENCE SIGNS LIST

1 Smartphone (portable terminal)
2 Camera
3 Control unit
3a Light on/off control unit
3b Photography control means
3c Display control means
10 Lens (lens module) for skin
12 LED (light source) for blot photographing
13 LED (light source) for texture photographing
16 CPU (light source control means)

The invention claimed is:

1. A portable photography device, comprising:
a portable terminal with a camera; and
a lens module that is removably installed on the portable terminal,
the lens module including
multiple types of light sources to irradiate an object,
a conversion lens that collects reflected light emitted from the light sources and reflected on the object, and
a first processor that carries out on/off control of the multiple types of light sources in a predetermined blink mode, and the portable terminal including a second processor configured to implement:
a detection unit that detects on/off states of the light sources by analyzing an image taken with the camera, and
a photography control unit that controls photography by the camera to capture a still image when the detection unit detects the on state or the off state of the light sources.

2. The portable photography device according to claim 1, wherein
the first processor carries out on/off control of the multiple types of light sources in turn.

3. The portable photography device according to claim 2, wherein
the multiple types of light sources each have a different wavelength for each type of the light source,
the detection unit detects which type of light source is currently turned on by analyzing a color component of the photographed image, and the photography control unit controls the photography by the camera in synchronization with the light source that is currently turned on when the detection unit individually detects lighting of the light sources.

4. The portable photography device according to claim 1, wherein
the first processor controls each of the multiple types of light sources to be turned on in turn for a predetermined time period after all the light sources are turned off for a predetermined time period.

5. The portable photography device according to claim 4, wherein
the photography control unit controls the photography by the camera in synchronization with the light source that is currently turned on when the detection unit detects lighting of the light source first time after detecting turning off of all the light sources, and
the photography control unit subsequently controls the photography by the camera in synchronization with lighting of a next type of the light source to be turned on.

6. The portable photography device according to claim 1, wherein
the first processor carries out control to alternately repeat a state in which all the light sources are turned off for a predetermined time period and a state in which one of the multiple types of light sources is turned on.

7. The portable photography device according to claim 6, wherein
the photography control unit controls the photography by the camera in synchronization with the light source that is currently turned on when the detection unit detects lighting of the light source after detecting turning off of all the light sources.

8. The portable photography device according to claim 1, the second processor is further configured to implement:
a display control unit that displays the photographed image taken by the camera according to the control of the photography control unit on a screen of the portable terminal in relation to the type of the light source, based on the detection of the predetermined blink mode by the detection unit.

9. The portable photography device according to claim 8, wherein
the multiple types of light sources include a light source for texture photographing and a light source for blot photographing, and
the second processor is further configured to implement:
the display control unit further displays a photographed image taken by the camera with the light source for texture photographing and a photographed image taken by the camera with the light source for blot photographing, both photographed images being taken according to the control of the photography control unit, as a photographed texture image and a photographed blot image, respectively, on the screen of the portable terminal.

10. The portable photography device according to claim 1, wherein:
the multiple types of light sources each have a different wavelength for each type of the light source, and
the second processor is further configured to implement:
a display control unit that displays the photographed image taken by the camera according to the control of the photography control unit on a screen of the portable terminal in relation to the type of the light source, based on the color component of the photographed image.

11. The portable photography device according to claim 10, wherein
the multiple types of light sources include a light source for texture photographing and a light source for blot photographing, and
the second processor is further configured to implement:

the display control unit further displays a photographed image taken by the camera with the light source for texture photographing and a photographed image taken by the camera with the light source for blot photographing, both photographed images being taken according to the control of the photography control unit, as a photographed texture image and a photographed blot image, respectively, on the screen of the portable terminal based on the color component of each of the photographed images.

12. The portable photography device according to claim 1, wherein
the first processor controls each of the multiple types of light sources to be turned on in turn for a predetermined time period after all the light sources are turned off for a predetermined time period,
the photography control unit controls the photography by the camera in synchronization with the light source that is currently turned on when the detection unit detects lighting of the light source first time after detecting turning off of all the light sources, and
the photography control unit subsequently controls the photography by the camera in synchronization with lighting of a next type of the light source to be turned on.

13. The portable photography device according to claim 1, wherein
the first processor carries out control to alternately repeat a state in which all the light sources are turned off and a state in which one of the multiple types of light sources is turned on by changing the type of the light source to be lighted, and
the photography control unit controls the photography by the camera in synchronization with the light source that is currently turned on when the detection unit detects lighting of the light source after detecting turning off of all the light sources.

14. The portable photography device according to claim 1, wherein
the multiple types of light sources each have a different wavelength for each type of the light source,
the first processor carries out on/off control of the multiple types of light sources in turn,
the detection unit detects which type of light source is currently turned on by analyzing a color component of the photographed image, and
the photography control unit controls the photography by the camera in synchronization with the light source that is currently turned on when the detection unit individually detects lighting of the light sources.

15. A portable terminal with a camera to which a lens module is capable of being installed, the lens module including a plurality of light sources to irradiate an object, the portable terminal comprising:
a processor configured to implement:
a detection unit that detects on/off states of the light sources by analyzing an image taken with the camera;
a photography control unit that controls photography by the camera to capture a still image when the detection unit detects the on state or the off state of the light sources; and
a display control unit that associates a photographed image taken by the camera according to the control of the photography control unit with the types of the light sources and displays the photographed image on the screen of the portable terminal.

\* \* \* \* \*